(12) United States Patent
Wakana et al.

(10) Patent No.: US 10,883,949 B2
(45) Date of Patent: Jan. 5, 2021

(54) MOISTURE DETECTION ELEMENT, GAS DETECTION DEVICE, AND BREATH INSPECTION SYSTEM

(71) Applicant: Hitachi, Ltd., Tokyo (JP)

(72) Inventors: Hironori Wakana, Tokyo (JP); Masuyoshi Yamada, Tokyo (JP); Minoru Sakairi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 267 days.

(21) Appl. No.: 15/767,509

(22) PCT Filed: Oct. 15, 2015

(86) PCT No.: PCT/JP2015/079115
§ 371 (c)(1),
(2) Date: Apr. 11, 2018

(87) PCT Pub. No.: WO2017/064784
PCT Pub. Date: Apr. 20, 2017

(65) Prior Publication Data
US 2018/0284048 A1 Oct. 4, 2018

(51) Int. Cl.
*G01N 27/12* (2006.01)
*G01N 33/497* (2006.01)
(Continued)

(52) U.S. Cl.
CPC ......... *G01N 27/121* (2013.01); *G01N 27/048* (2013.01); *G01N 27/22* (2013.01);
(Continued)

(58) Field of Classification Search
CPC .. G01N 27/121; G01N 27/048; G01N 27/223; G01N 27/22; G01N 33/4972
See application file for complete search history.

(56) References Cited

U.S. PATENT DOCUMENTS 4,809,810 A * 3/1989 Elfman .............. G01N 33/4972
180/272
2005/0008061 A1 1/2005 Kaneko
(Continued)

FOREIGN PATENT DOCUMENTS

EP 1 496 353 A1 1/2005
GB 2 022 837 A 12/1979
(Continued)

OTHER PUBLICATIONS

International Search Report (PCT/ISA/210) issued in PCT Application No. PCT/JP2015/079115 dated Jan. 12, 2016 with English-language translation (five (5) pages).
(Continued)

Primary Examiner — Eric S. McCall
Assistant Examiner — Timothy P Graves
(74) Attorney, Agent, or Firm — Crowell & Moring LLP

(57) ABSTRACT

In order to provide a moisture detection element, a gas detection device, and a breath inspection system that are compact and have high response performance, the moisture detection element includes an insulating section made of an insulating material, an application electrode to which an voltage is applied, and a detection electrode that detects a voltage signal corresponding to a current flowing through an electrical path via water molecules adsorbed on the insulating section by the voltage applied to the application electrode.

11 Claims, 18 Drawing Sheets

(51) Int. Cl.
   *G01N 27/22* (2006.01)
   *G01N 33/00* (2006.01)
   *G01N 27/04* (2006.01)

(52) U.S. Cl.
   CPC ......... *G01N 27/223* (2013.01); *G01N 27/225* (2013.01); *G01N 33/004* (2013.01); *G01N 33/005* (2013.01); *G01N 33/0031* (2013.01); *G01N 33/0037* (2013.01); *G01N 33/0047* (2013.01); *G01N 33/497* (2013.01); *G01N 33/4972* (2013.01)

(56) References Cited

U.S. PATENT DOCUMENTS

| | | | |
|---|---|---|---|
| 2006/0096370 A1 | 5/2006 | Isogai et al. | |
| 2010/0307238 A1* | 12/2010 | Van Popta | G01N 27/225 73/335.04 |
| 2011/0102182 A1* | 5/2011 | Ohya | G01N 33/497 340/576 |
| 2012/0037799 A1 | 2/2012 | Sakairi | |
| 2015/0068302 A1* | 3/2015 | Koo | G01N 27/223 73/335.04 |
| 2017/0241931 A1* | 8/2017 | Kitazawa | G01N 27/12 |

FOREIGN PATENT DOCUMENTS

| | | | |
|---|---|---|---|
| JP | 54-139097 A | | 10/1979 |
| JP | 2-228546 A | | 9/1990 |
| JP | 7-20074 A | | 1/1995 |
| JP | 11-218580 A | | 8/1999 |
| JP | 2009-136393 A | | 6/2009 |
| JP | 2011053049 | * | 9/2009 |
| JP | 4455286 B2 | | 4/2010 |
| JP | 2011-53049 A | | 3/2011 |
| JP | 2011-95212 A | | 5/2011 |
| JP | 5254432 B2 | | 8/2013 |
| JP | 2015-513664 A | | 5/2015 |
| WO | WO 2014/110159 A1 | | 7/2014 |

OTHER PUBLICATIONS

Japanese-language Written Opinion (PCT/ISA/237) issued in PCT Application No. PCT/JP2015/079115 dated Jan. 12, 2016 (five (5) pages).

Extended European Search Report issued in counterpart European Application No. 15906248.8 dated Jun. 13, 2019 (eight (8) pages).

Japanese-language Office Action issued in counterpart Japanese Application No. 2017-545046 dated Jun. 4, 2019 with English translation nine (9) pages).

* cited by examiner

[FIG. 1A]
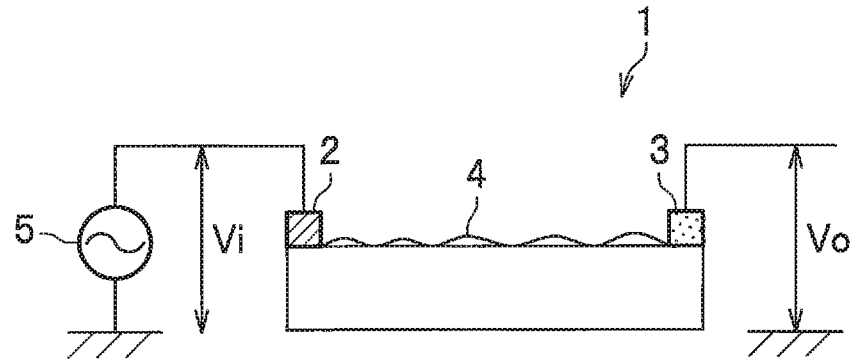
[FIG. 1B]
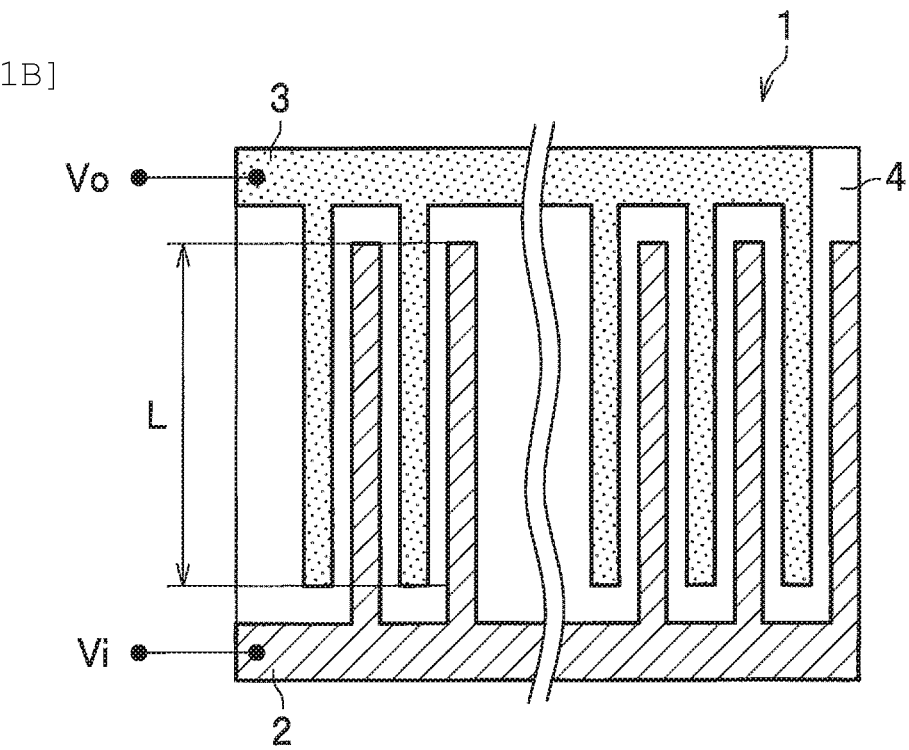

[FIG. 2A]
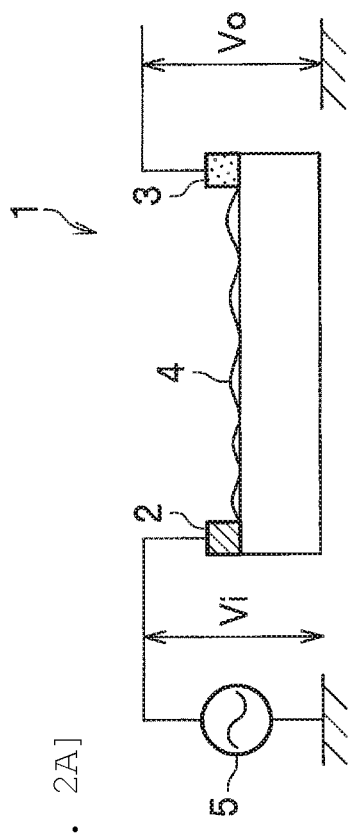
[FIG. 2B]
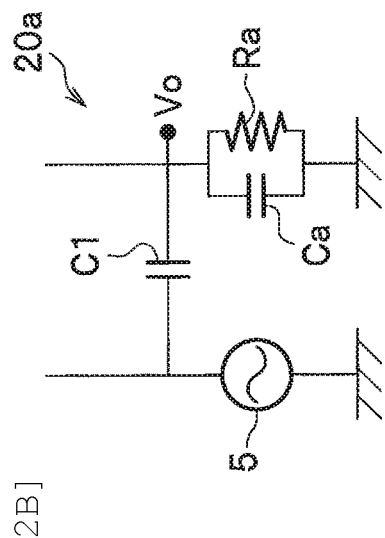
[FIG. 2C]
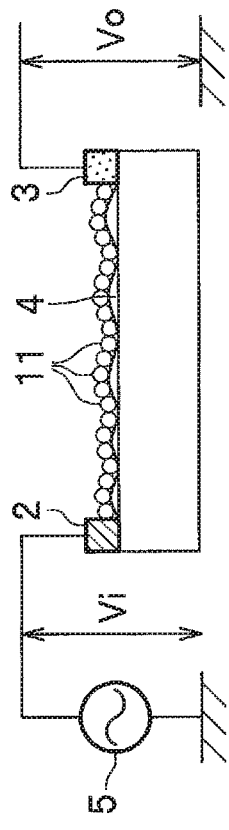
[FIG. 2D]
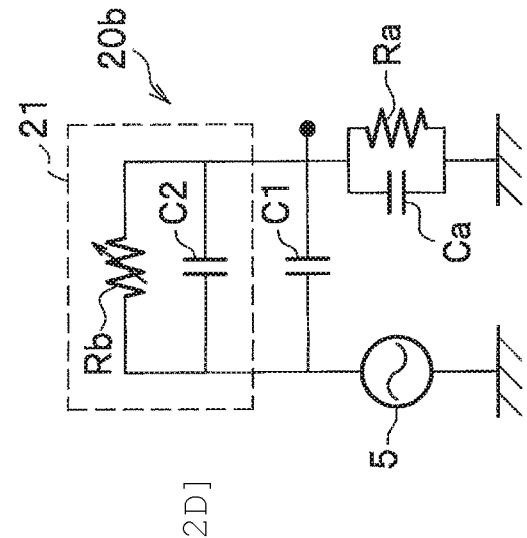

[FIG. 3]
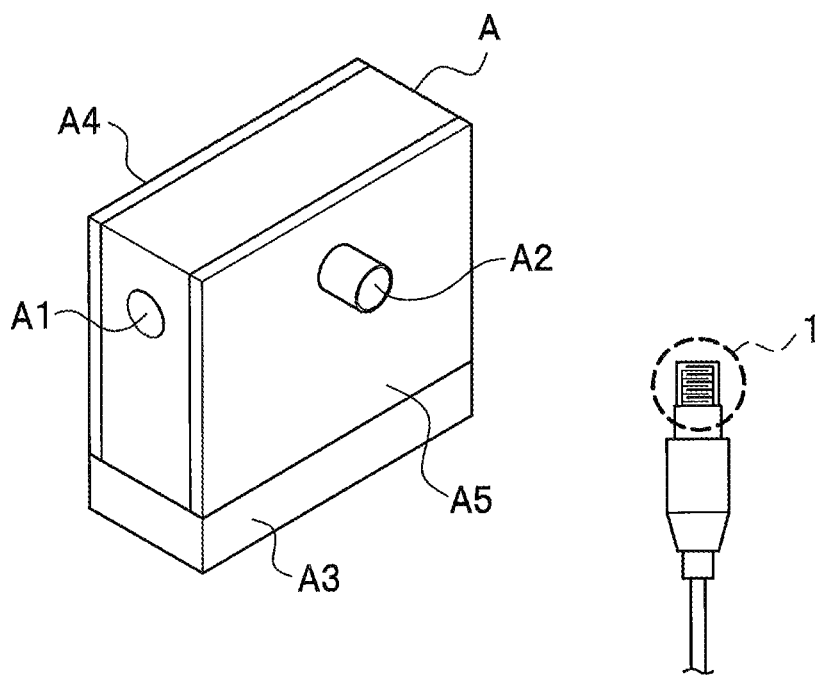

[FIG. 4]
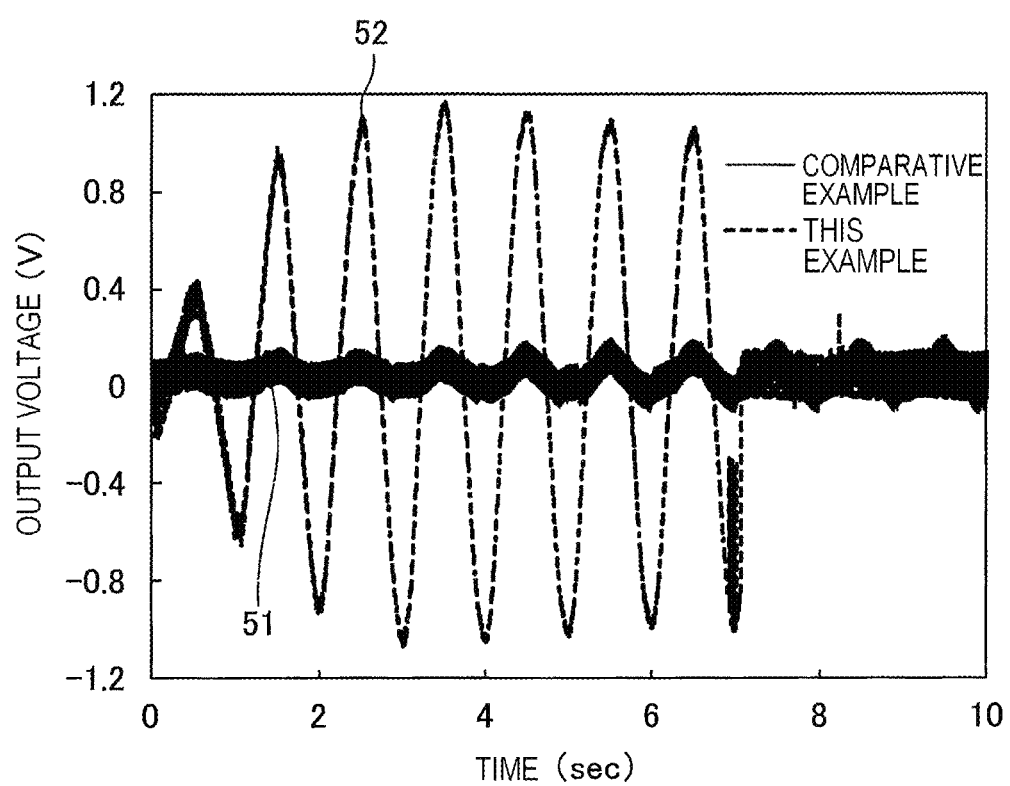

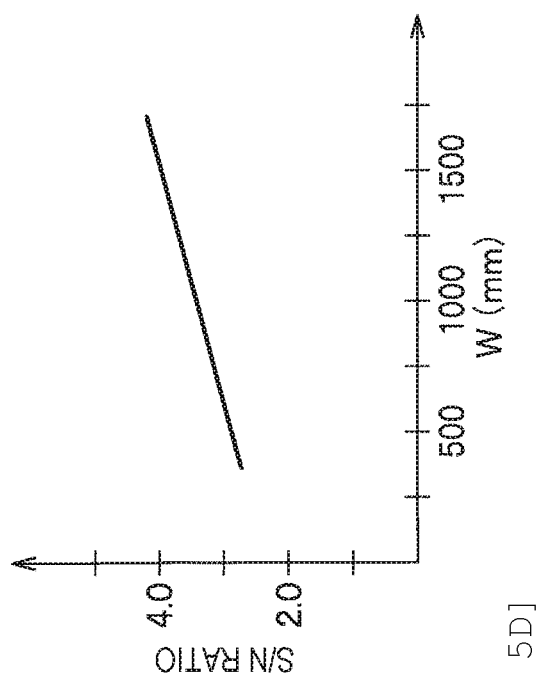
[FIG. 5A]
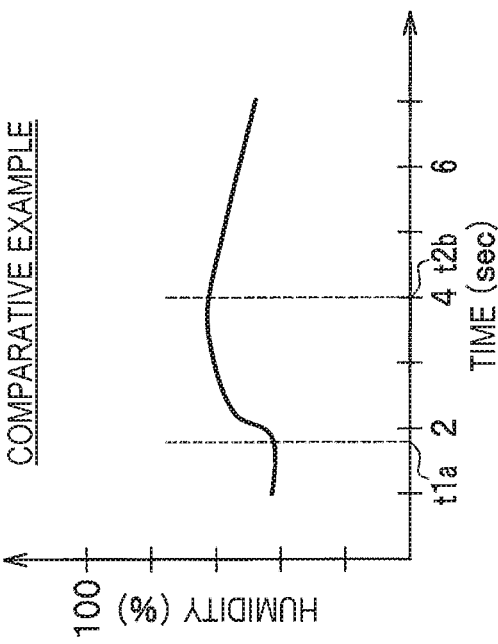
[FIG. 5B]
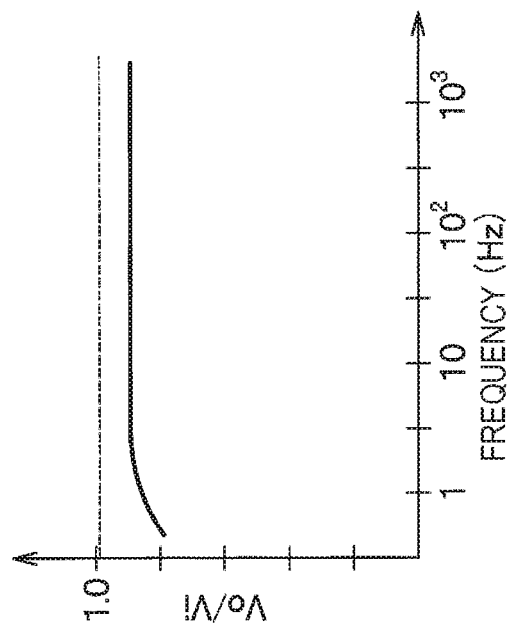
[FIG. 5C]
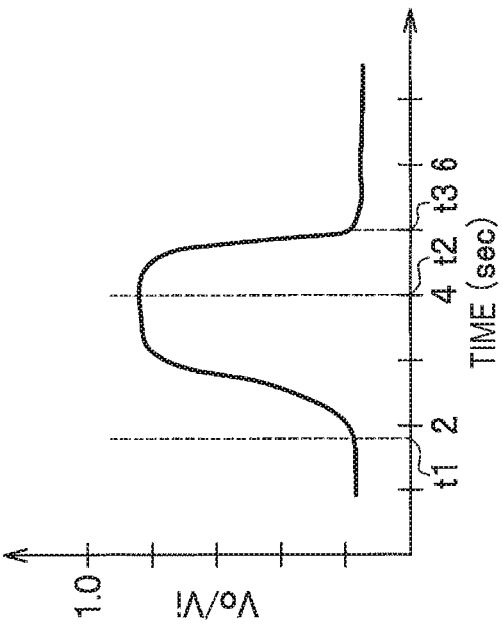
[FIG. 5D]

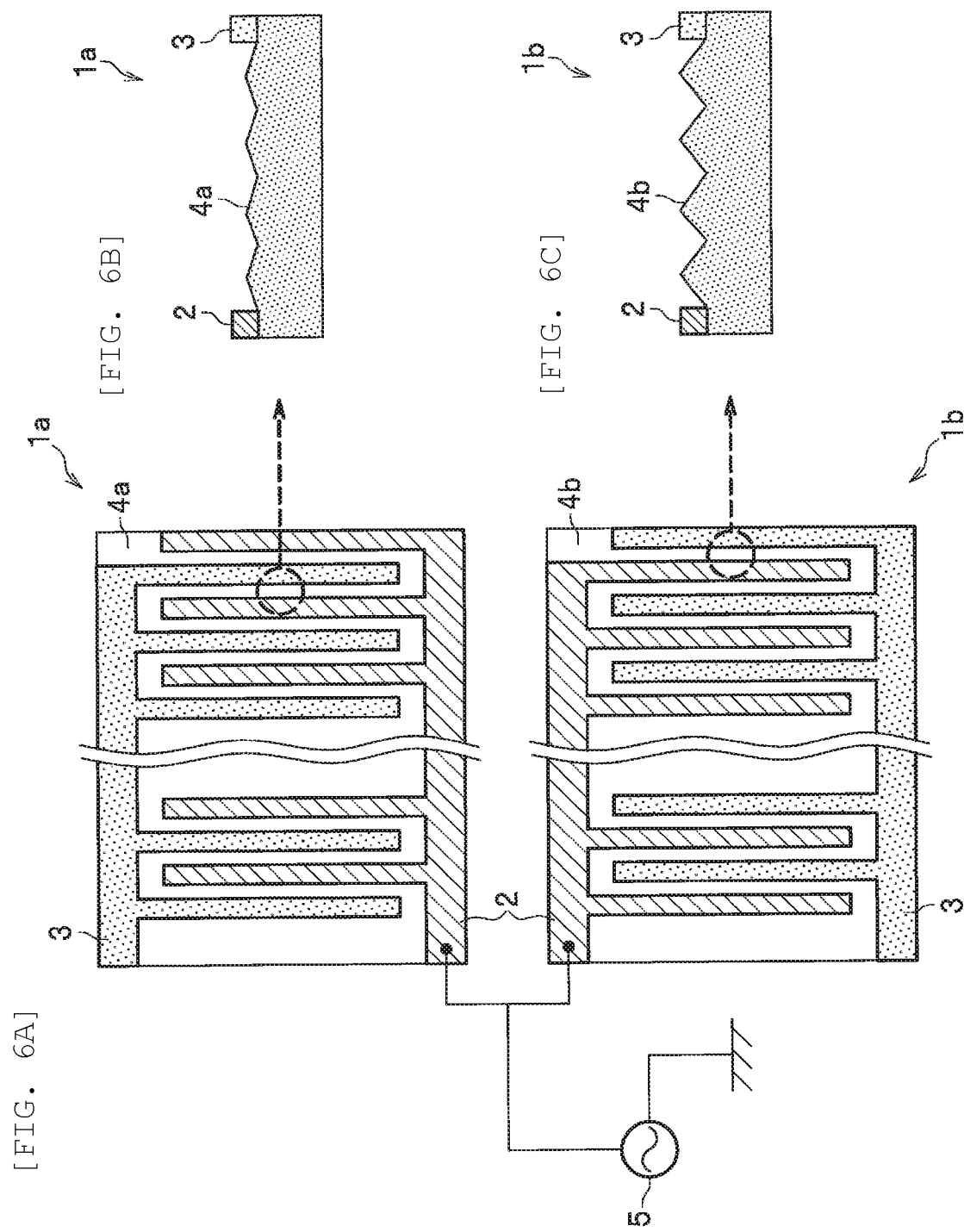

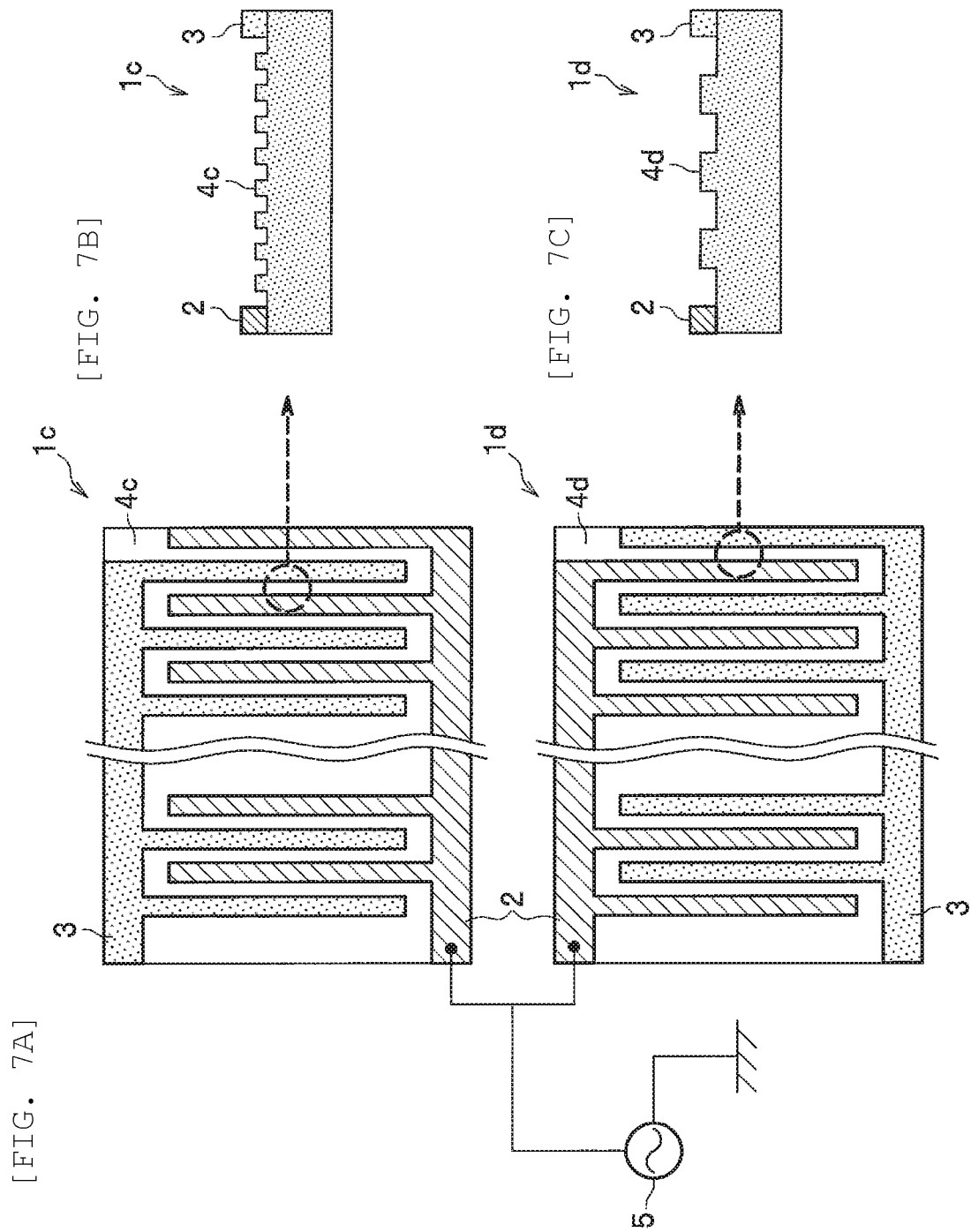

[FIG. 8A] PROCESSING TREATMENT
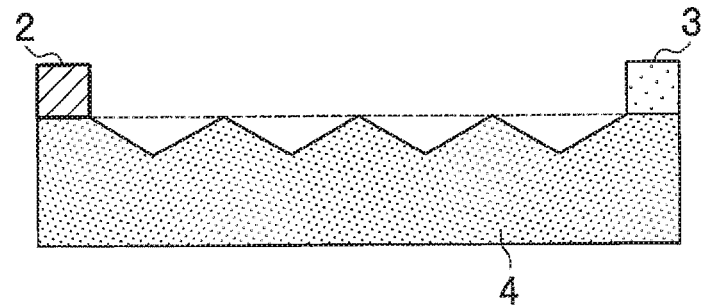
[FIG. 8B] AMORPHOUS TREATMENT
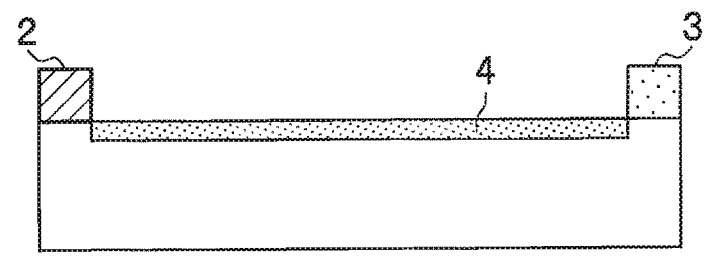
[FIG. 8C] PRINTING TREATMENT
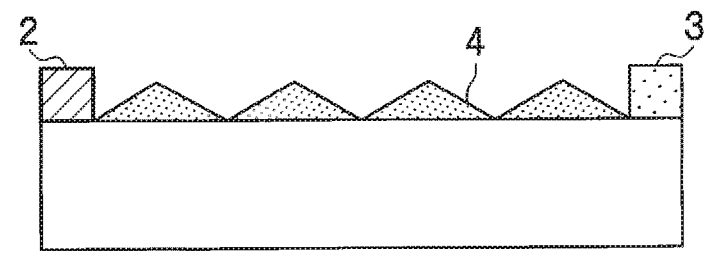

[FIG. 9]
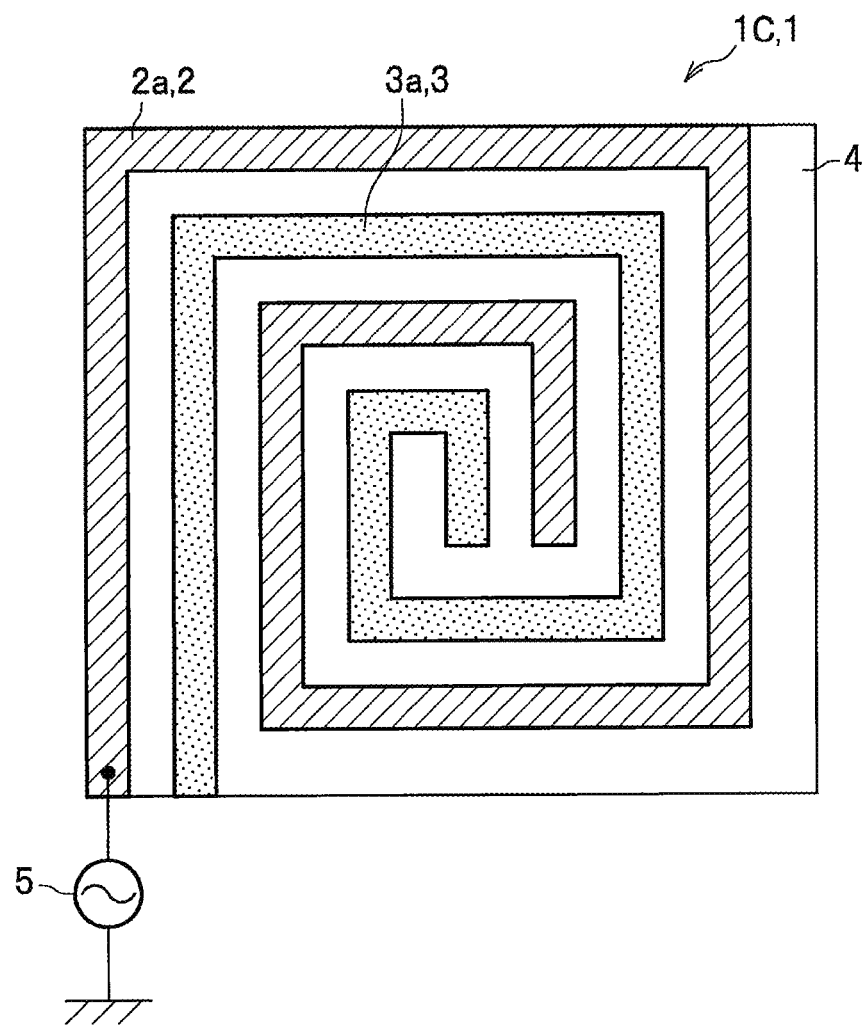

[FIG. 10]
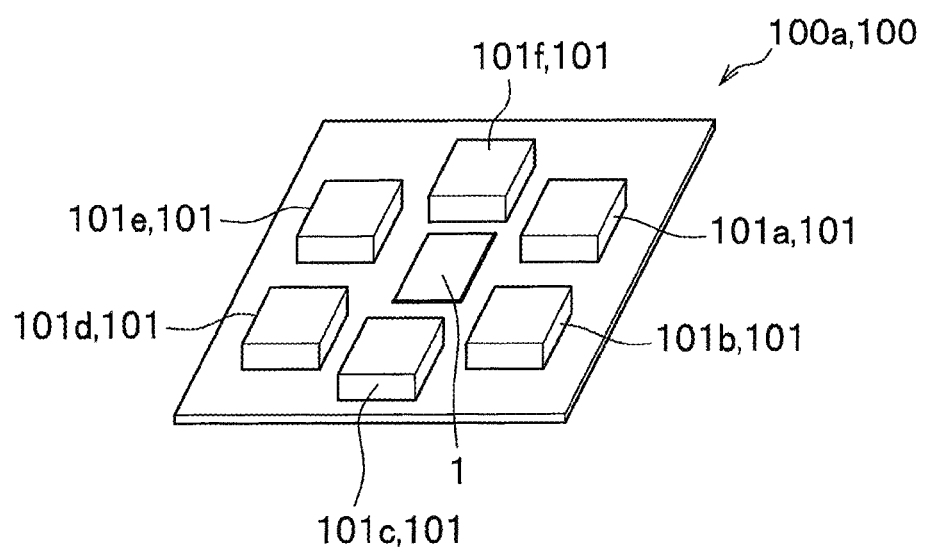

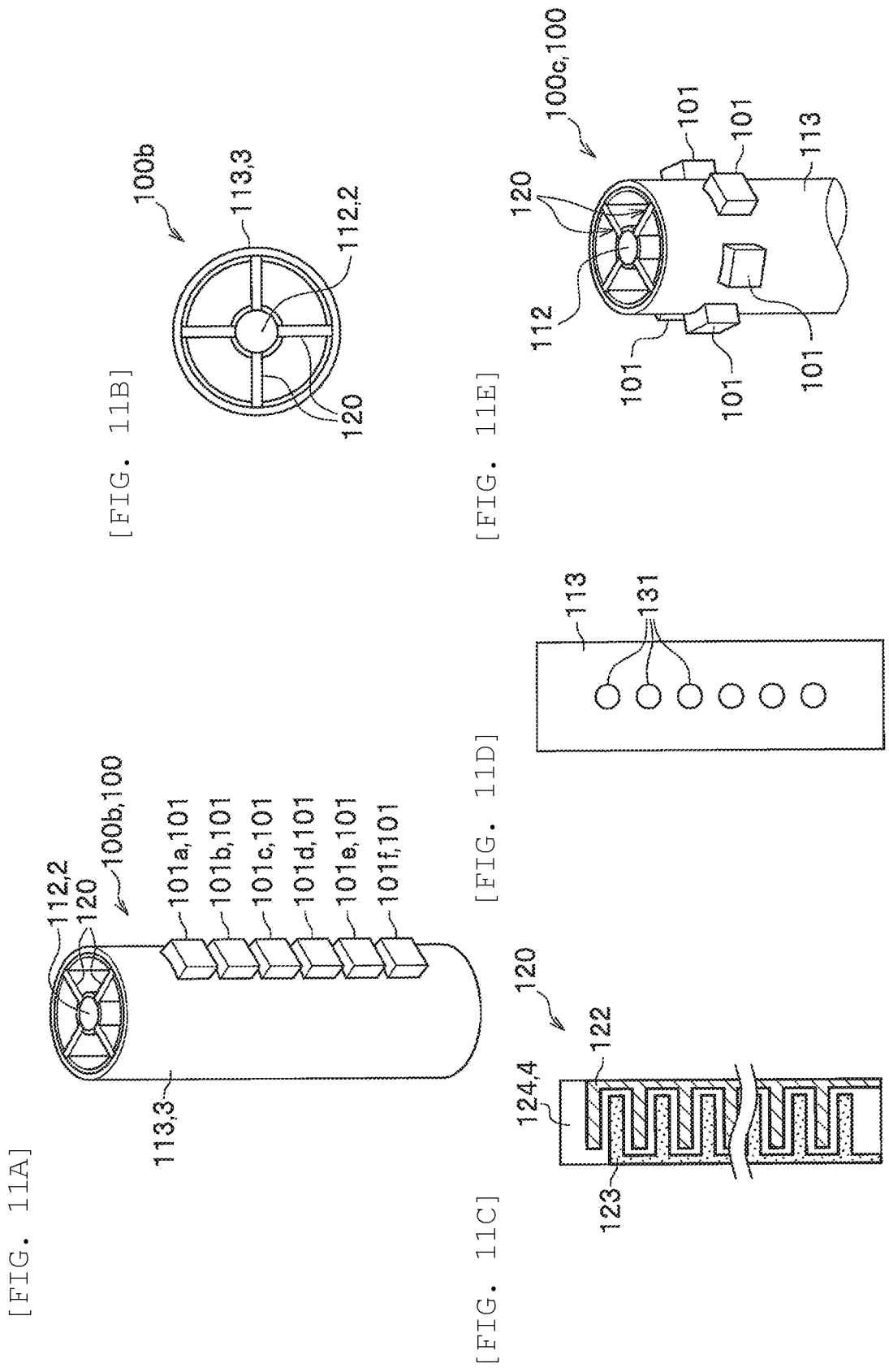

[FIG. 12]
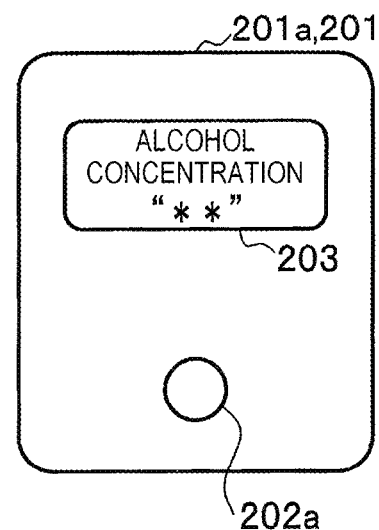
[FIG. 13]
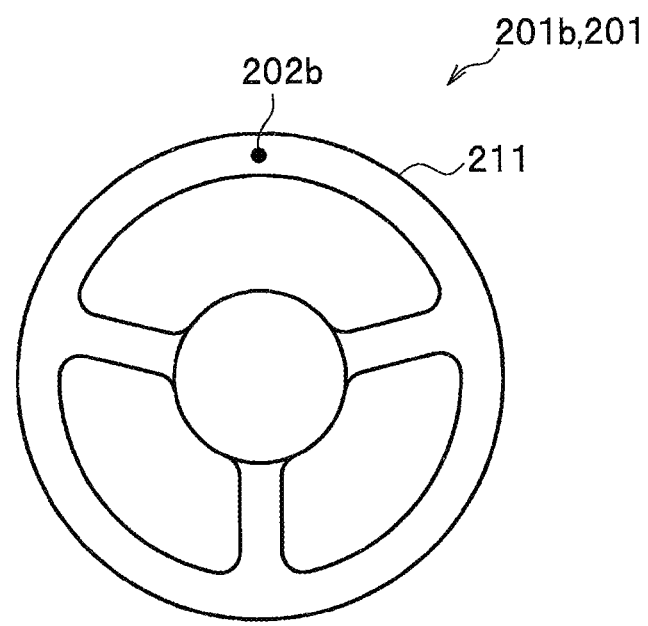

[FIG. 14]
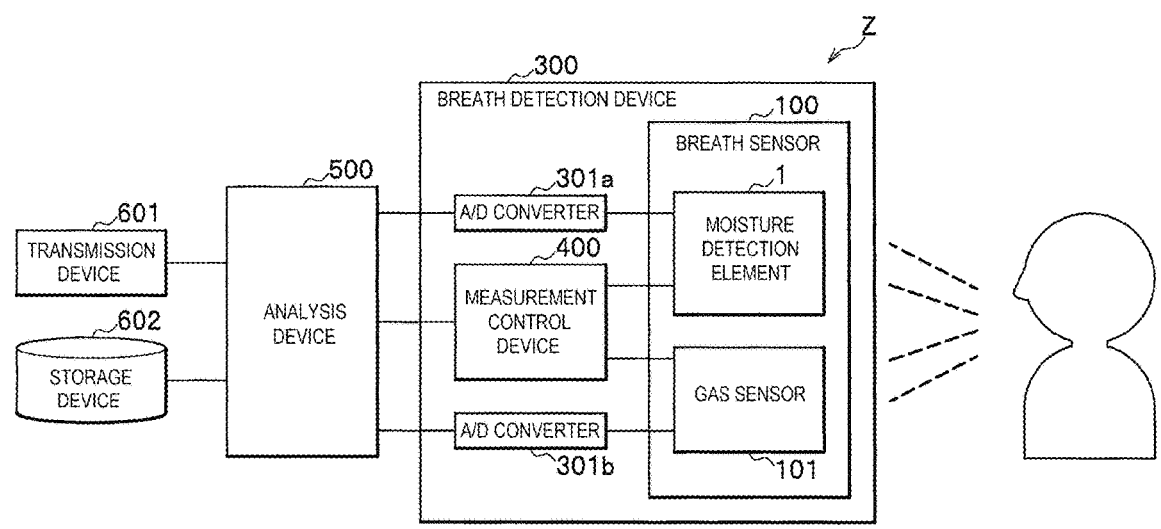

[FIG. 15]
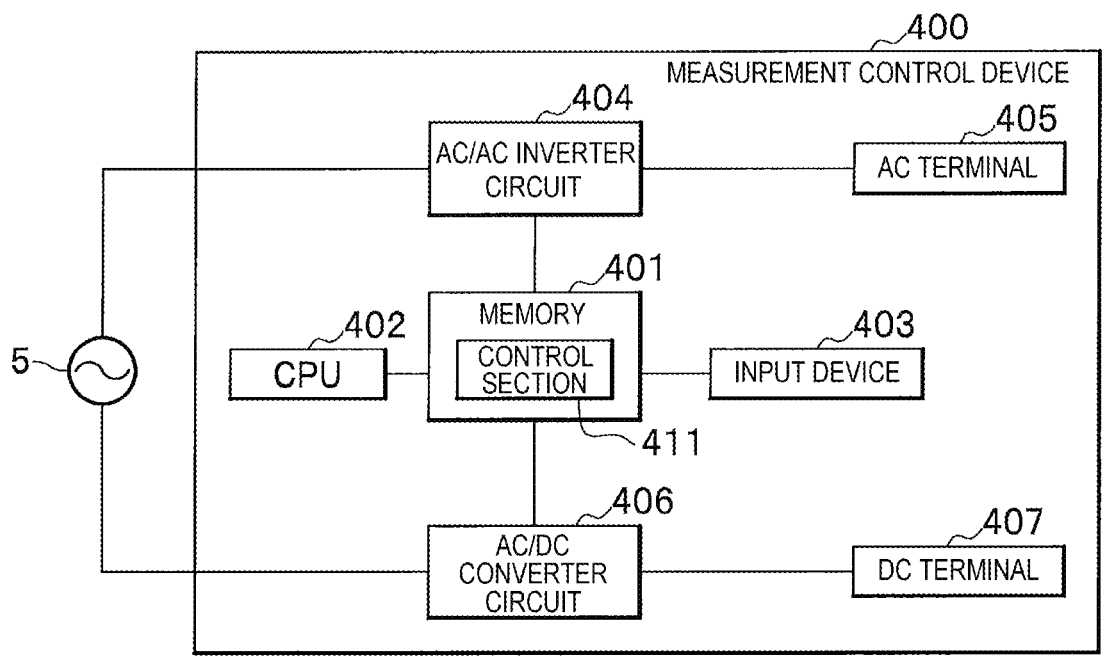
[FIG. 16]
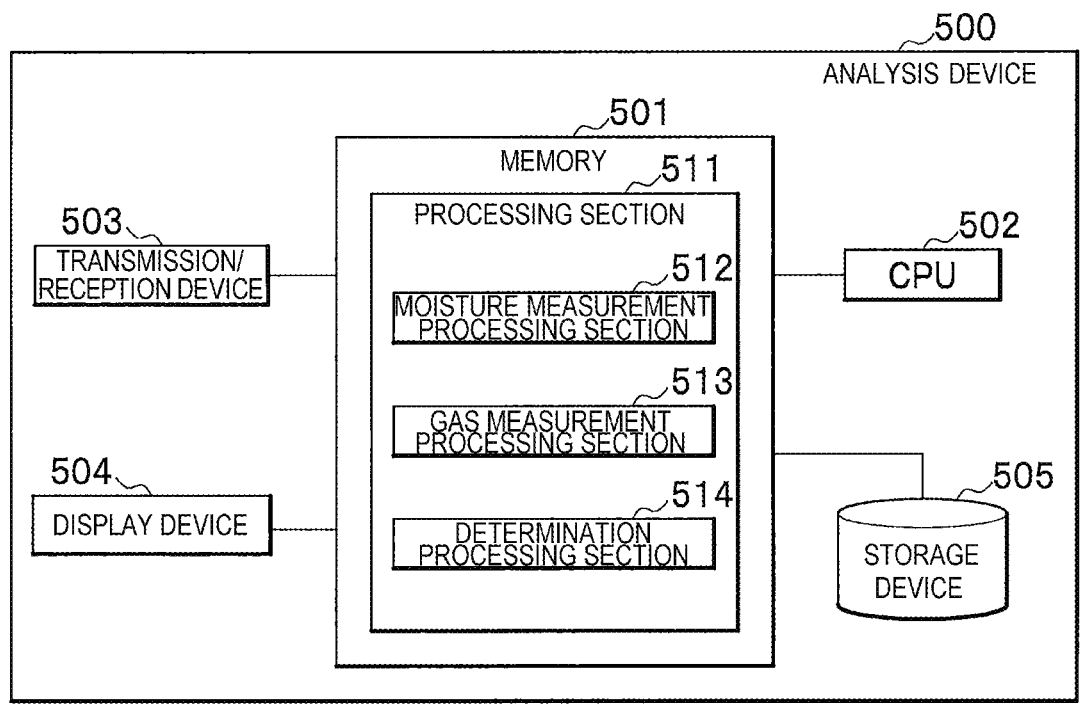

[FIG. 17]
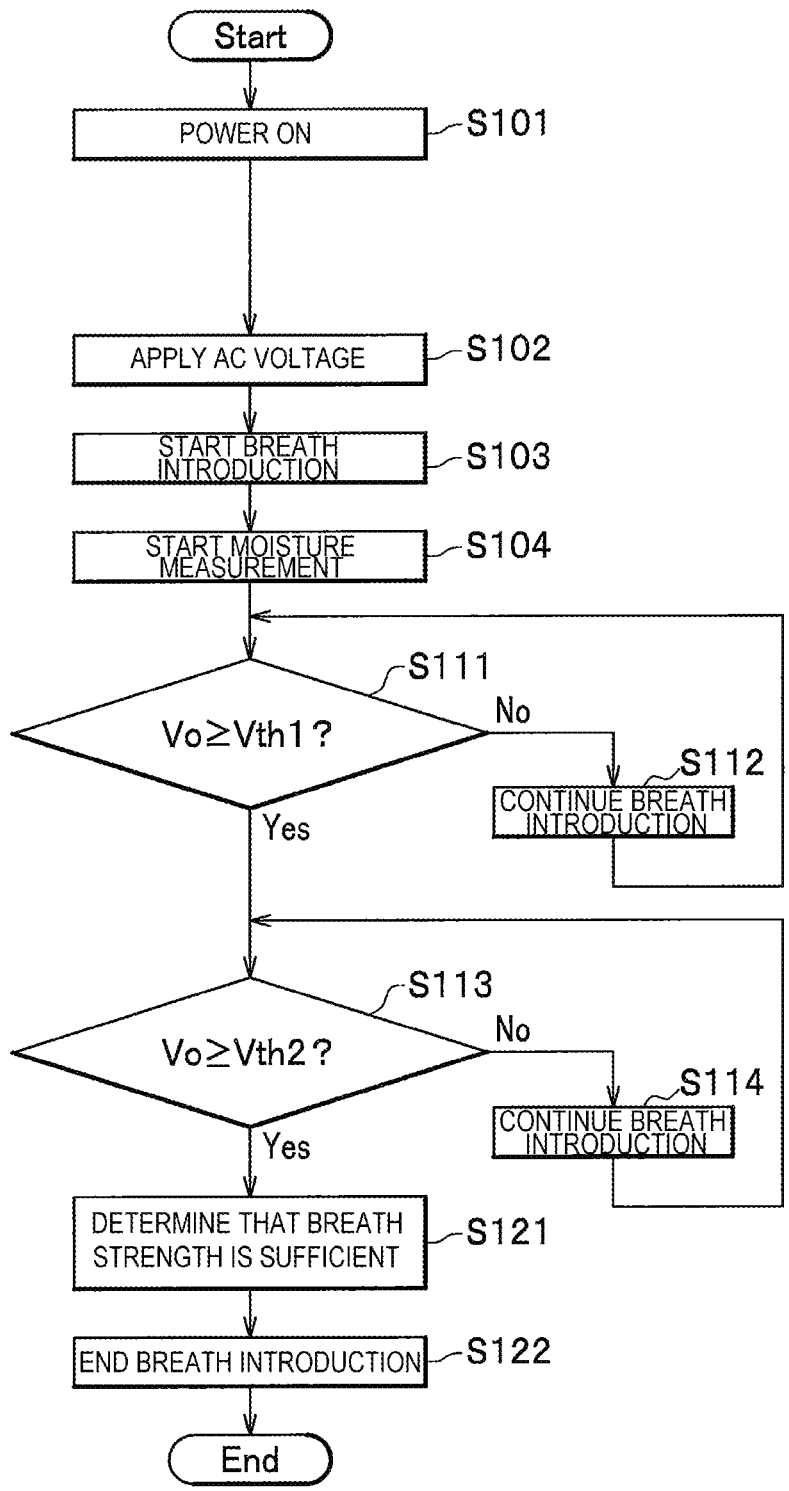

[FIG. 18]
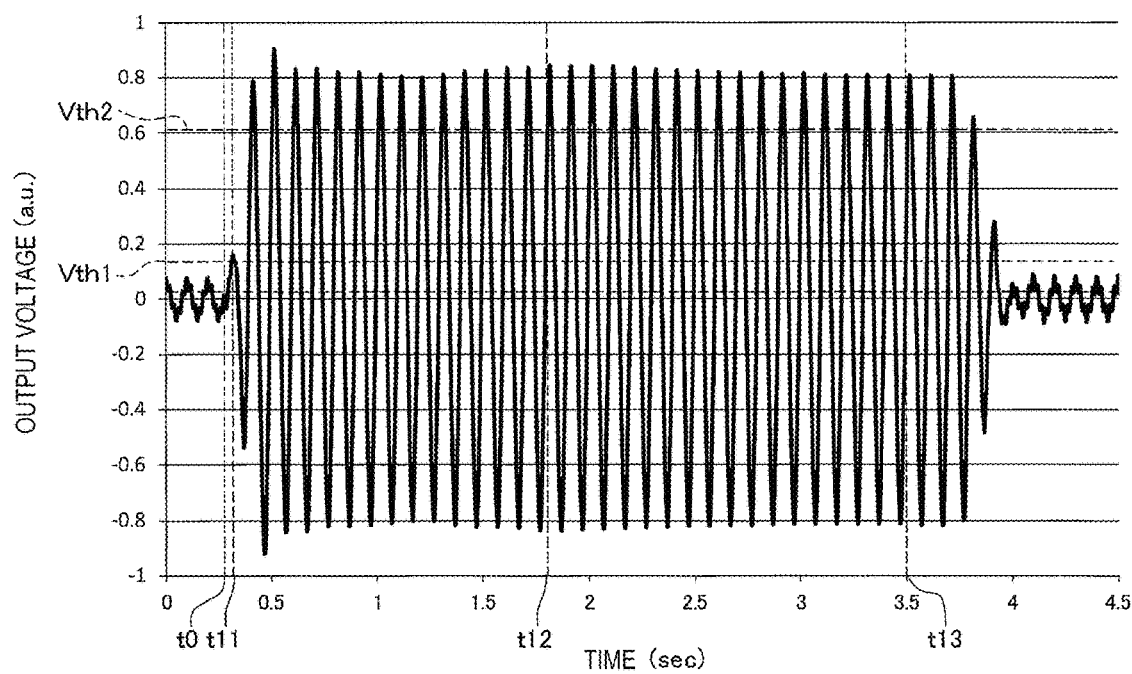

[FIG. 19]
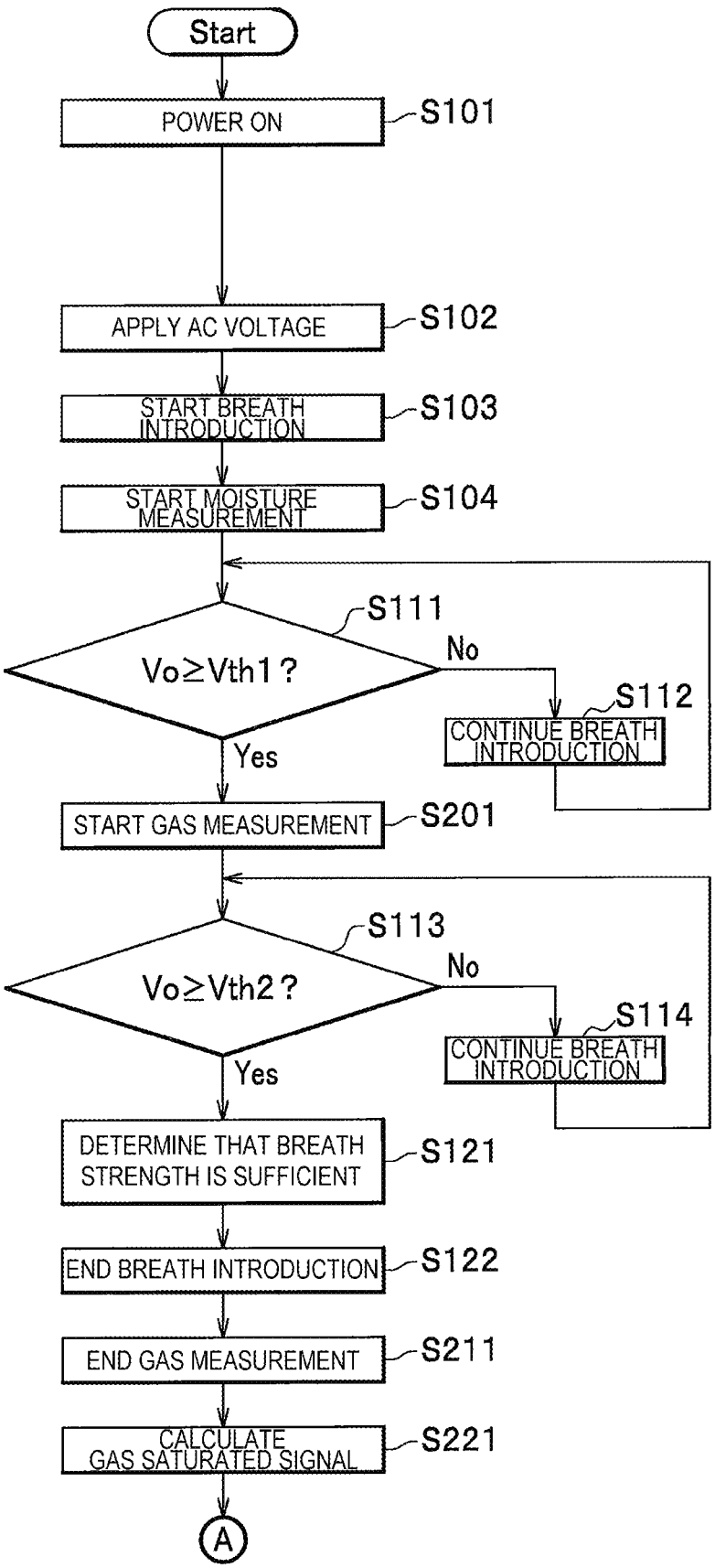

[FIG. 20]
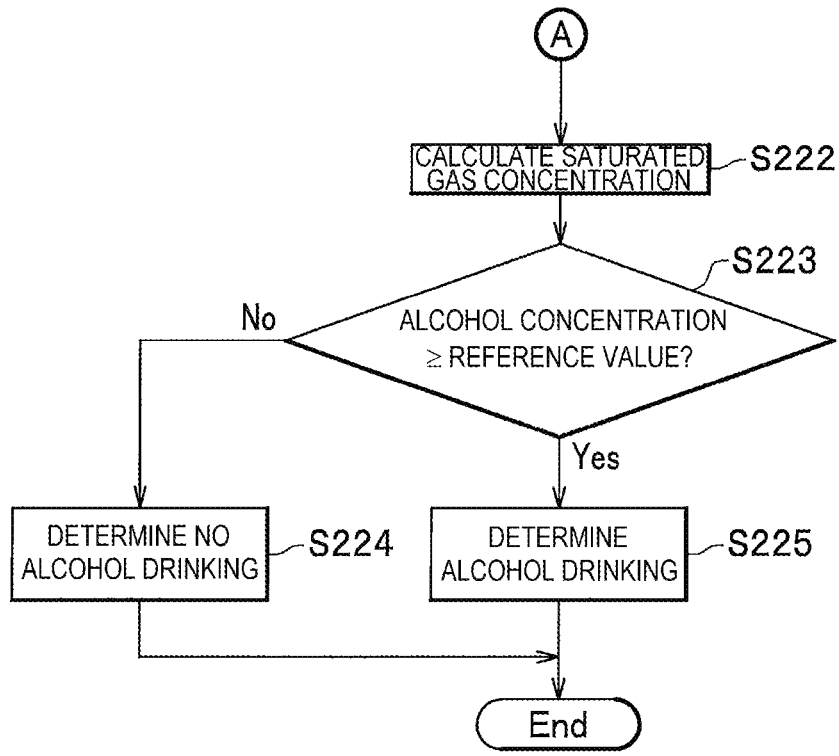
[FIG. 21]
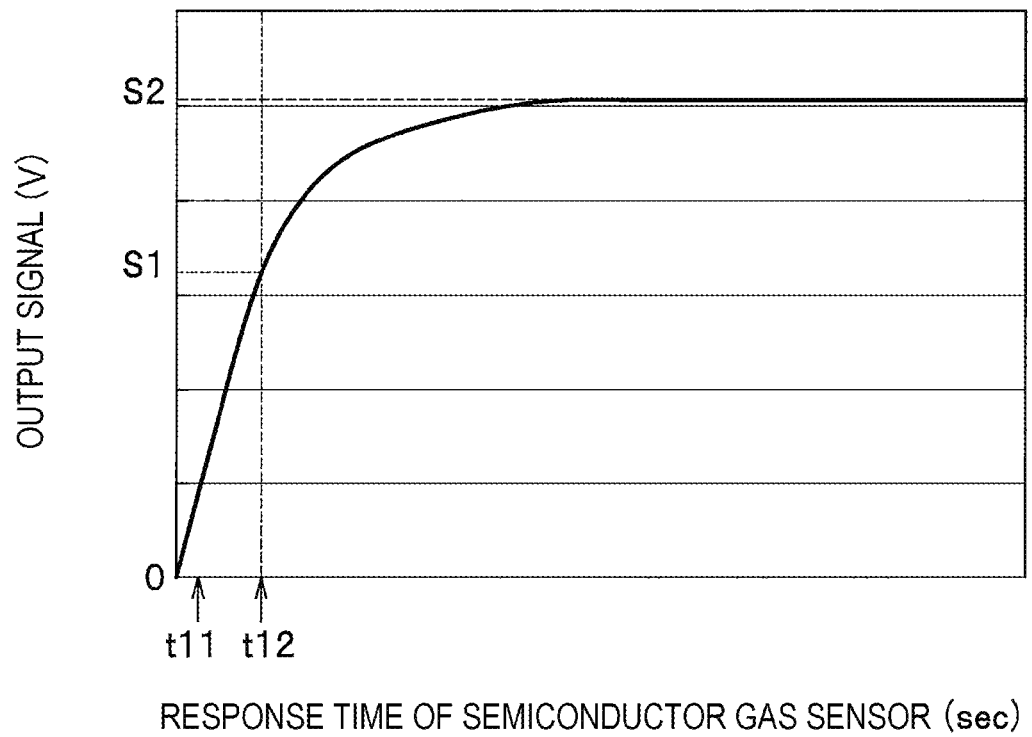
RESPONSE TIME OF SEMICONDUCTOR GAS SENSOR (sec)

MOISTURE DETECTION ELEMENT, GAS DETECTION DEVICE, AND BREATH INSPECTION SYSTEM

TECHNICAL FIELD

The present invention relates to a technique for a moisture detection element for detecting moisture in a breath, a gas detection device, and a breath inspection system.

BACKGROUND ART

Drivers of business vehicles are required to undergo alcohol inspection in order to eradicate accidents due to drunk driving.

Here, conventional alcohol inspection devices measure an alcohol content in a breath of a subject through introduction of the breath into the device. Since a breath that is not exhaled from a human can be measured in such an alcohol inspection device, there possibly arise impersonations and the like by the subject blowing external air or the like instead of his/her own breath.

For preventing such impersonations, it is required to inspect whether the air introduced into the alcohol inspection device is a breath. Since human breath is saturated with water vapor unlike external air, by measuring the water vapor content in the air introduced into the alcohol inspection device, that is, by measuring the moisture, it is possible to judge whether the introduced air is a human breath, thereby preventing impersonations.

As an example of such a moisture measurement device, a capacitive humidity sensor is disclosed in PTL 1. PTL 1 discloses "a capacitance humidity sensor for detecting a humidity change in an atmosphere using a capacitance change, the capacitance humidity sensor including a first sensor element and a second sensor element on which a humidity sensitive film having a dielectric constant which changes in accordance with the humidity change is formed, the first sensor element having a capacitance and a changing rate of the capacitance with respect to a humidity change that are different from those of the second sensor element, wherein the first sensor element and the second sensor element each are a comb-teeth electrode type capacitive element including a pair of comb-teeth electrodes which are formed on one plain surface on a semiconductor substrate via an insulating film using a wiring step for forming semiconductor elements at different positions of the semiconductor substrate, and which are disposed so as to face each other with a gap therebetween with the comb-teeth portions mated with each other, wherein the first sensor element is connected with the second sensor element in series, and wherein the humidity sensitive film is formed on the semiconductor substrate so as to cover the pair of comb-teeth electrodes of each of the first and second sensor elements via a protective film for wiring the semiconductor elements on the semiconductor substrate, and wherein the first and second sensor elements each are composed of the semiconductor substrate, the insulating film, the pair of comb-teeth electrodes, the protective film, and the humidity sensitive film, a distance between the comb-teeth portions of the pair of comb-teeth electrodes of the first sensor being different from that of the second sensor element" (see claim 1).

As another example, an ion detection sensor is disclosed in PTL 2. PTL 2 discloses "an ion detection device having a housing, the inside of the housing being under an atmospheric environment, the device including in the housing: an ion source for generating an ion beam; opposite electrodes each having an opening, the beam passing through the opening; an introduction means for introducing external air into the housing; and a detection electrode for detecting ions that are deflected into the gravity direction through a reaction of the ion beam with the external air introduced into the housing by the introduction means, wherein the device is provided with an exhaust means on the downstream side of the opposite electrodes in the ion beam irradiation direction and at a level lower than the openings of the opposite electrodes" (see claim 1).

CITATION LIST

Patent Literature

PTL 1: Japanese Patent No. 4455286
PTL 2: Japanese Patent No. 5254432

SUMMARY OF INVENTION

Technical Problem

However, since the technique described in PTL 1 uses a moisture sensitive film, there is a problem in that it takes a time of about one minute to detect moisture and further complete the measurement of the moisture. Accordingly, the technique has a problem in that it is difficult to make the determination while a human exhales a breath.

In addition, since the output is small in the technique described in PTL 2, the technique has a problem in that the output has to be amplified, resulting in large power consumption.

The techniques described in PTLs 1 and 2 have a problem of difficulty of size reduction. Mobile-type inspection terminals suitable for various application cases are increasingly demanded in the market, and therefore, also in terms of the need to respond to the spread of mobile equipment, the sizes of such moisture measurement devices are essentially to be reduced.

The present invention has been made against the background, and an object of the present invention is to provide a moisture detection element, a gas detection device, and a breath inspection system that are compact and have high response performance.

Solution to Problem

For solving the above problems, the present invention is characterized by including an insulating section made of an insulating material, an application section to which a voltage is applied, and an outputting section that outputs a voltage signal corresponding to a current flowing through an electrical path via water molecules adsorbed on a surface of the insulating material by the voltage applied to the application section.

Other solving means will be appropriately described in embodiments.

Advantageous Effects of Invention

The present invention can provide a moisture detection element, a gas detection device, and a breath inspection system that are compact and have high response performance.

BRIEF DESCRIPTION OF DRAWINGS

FIGS. 1A and 1B illustrate a structure of a moisture detection element according to this embodiment. FIG. 1A is a schematic view illustrating the principle of the moisture detection element and FIG. 1B is a schematic top view of the moisture detection element.

FIGS. 2A to 2D are diagrams for explaining the principle of moisture detection by the moisture detection element of the embodiment. FIG. 2A is a schematic view illustrating the principle of the moisture detection element before moisture deposition, FIG. 2B shows an equivalent circuit of the moisture detection element before moisture deposition, FIG. 2C is a schematic view illustrating the principle of the moisture detection element after moisture deposition, and FIG. 2D shows an equivalent circuit of the moisture detection element after moisture deposition.

FIG. 3 is a view for comparing the size of a moisture detection element in a comparative example with that of the moisture detection element of the embodiment.

FIG. 4 is a graph showing a comparison in output of the ion detection sensor in the comparative example and the moisture detection element of the embodiment.

FIGS. 5A to 5D are graphs for explaining characteristics of the moisture detection element of the embodiment. FIG. 5A shows a frequency characteristic, FIG. 5B shows a characteristic with respect to the electrode length, FIG. 5C shows a response characteristic, and FIG. 5D shows a response characteristic of a known technique as a comparative example.

FIGS. 6A to 6C show examples of a low temperature type and a high temperature type moisture detection elements according to the embodiments. FIG. 6A is a top view of the moisture detection elements, FIG. 6B is a schematic view illustrating the principle of the low temperature type moisture detection element, and FIG. 6C is a schematic view illustrating the principle of the high temperature type moisture detection element.

FIGS. 7A to 7C show another example of the low temperature type and high temperature type moisture detection elements according to the embodiment. FIG. 7A is a top view of the moisture detection elements, FIG. 7B is a schematic view illustrating the principle of the low temperature type moisture detection element, and FIG. 7C is a schematic view illustrating the principle of the high temperature type moisture detection element.

FIGS. 8A to 8C illustrate a method for forming a projections-and-depressions structure in an insulating section. FIG. 8A shows a processing treatment, FIG. 8B shows an amorphous treatment, and FIG. 8C shows a printing treatment.

FIG. 9 shows another example of the moisture detection element of the embodiment.

FIG. 10 shows an example of a breath sensor having a planar arrangement structure.

FIGS. 11A to 11E show examples of a breath sensor having a coaxial structure. FIG. 11A is an external perspective view of a breath sensor, FIG. 11B is a top view of the breath sensor, FIG. 11C illustrates a structure of the substrate section, FIG. 11D illustrates a structure of portions to which gas sensors are mounted, and FIG. 11E shows another example of the mounting direction of gas sensors.

FIG. 12 shows an example of a mobile type breath inspection device.

FIG. 13 shows an example of a breath inspection device incorporated in a steering wheel.

FIG. 14 shows an example of functional blocks of a breath inspection system according to the embodiment.

FIG. 15 is a functional block diagram showing a configuration example of a measurement control device according to the embodiment.

FIG. 16 is a functional block diagram showing a configuration example of an analysis device according to the embodiment.

FIG. 17 is a flowchart showing a procedure of a breath detection processing according to the embodiment.

FIG. 18 is a graph showing a temporal change of the output voltage.

FIG. 19 is a flowchart (No. 1) showing a procedure of a gas detection processing according to the embodiment.

FIG. 20 is a flowchart (No. 2) showing a procedure of the gas detection processing according to the embodiment.

FIG. 21 is a graph showing a temporal change of the output signal output from a gas sensor.

DESCRIPTION OF EMBODIMENTS

Next, modes for implementing the present invention (referred to as "embodiments") will be described in detail appropriately with reference to the drawings. Incidentally, in the drawings, identical signs are given to the respective similar components to omit the explanation. In addition, in the drawings, common signs are given to the respective common components to omit the explanation.

[Moisture Detection Element]
(Structure of Moisture Detection Element)

FIG. 1 illustrates a structure of a moisture detection element according to this embodiment in which (a) is a schematic view illustrating the principle of the moisture detection element and (b) is a schematic top view of the moisture detection element.

As shown in FIG. 1(a), a moisture detection element (moisture detection section) 1 includes an application electrode (application section) 2 that is connected to an AC power source 5 and to which an applied voltage Vi is applied by the AC power source 5, a detection electrode (outputting section) 3 that detects a potential Vo when detecting moisture, and an insulating section 4.

The insulating section 4 is composed of a substrate made of a hydrophilic insulating material, and at least the surface thereof is made of an oxide, specifically an insulating metal oxide or the like. Incidentally, the shape of the insulating section 4 is not necessarily a board shape.

As shown in FIG. 1(a), the insulating section 4 is interposed between the detection electrode 3 and the application electrode 2. Here, the insulating section 4 has a projections-and-depressions structure. The projections-and-depressions structure in the insulating section 4 will be described later.

(Principle of Moisture Detection)

FIG. 2 is a view for explaining the principle of moisture detection by the moisture detection element of the embodiment in which (a) is a schematic view illustrating the principle of the moisture detection element before moisture deposition, (b) shows an equivalent circuit of the moisture detection element before moisture deposition, (c) is a schematic view illustrating the principle of the moisture detection element after moisture deposition, and (d) shows an equivalent circuit of the moisture detection element after moisture deposition.

Incidentally, the configurations shown in FIG. 2(a) and FIG. 2(c) are the same as the configuration shown in FIG. 1(a), and therefore identical signs are given to omit the explanation.

As shown in FIG. 2(a), before moisture deposition, the detection electrode 3 and the application electrode 2 are connected via the insulating section 4 and therefore no current flows between the detection electrode 3 and the application electrode 2. Accordingly, although an AC voltage is applied to the application electrode 2, no voltage is detected from the detection electrode 3.

Then, when moisture is adsorbed on the insulating section 4 of the moisture detection element 1, as shown in FIG. 2(c), water molecules 11 are adsorbed on the insulating section 4. This allows a current to flow between the detection electrode 3 and the application electrode 2 with the water molecules 11 as a path. Then, a voltage applied to the application electrode 2 is detected (output) from the detection electrode 3. The moisture detection element 1 detects the moisture based on the detected (output) voltage.

Next, the states of the equivalent circuit 20 of the moisture detection element 1 are compared between before and after deposition of moisture.

Before the deposition of moisture, the equivalent circuit 20 is in the state of an equivalent circuit 20a as shown in FIG. 2(b). Here, a capacitor C1 represents the insulating section 4. Incidentally, since the distance between the detection electrode 3 and the application electrode 2 is sufficiently large, the capacitance of the capacitor C1 is a small value ($\ll 1$). Accordingly, the capacitive reactance of the equivalent circuit 20a shown in FIG. 2(b) is a large value, and almost no current flows between the detection electrode 3 and the application electrode 2.

Incidentally, a circuit composed of a capacitor Ca and a resistor Ra is an equivalent circuit of the atmospheric air.

Here, when moisture contained in a breath is adsorbed, the equivalent circuit 20a shown in FIG. 2(b) converts into an equivalent circuit 20b shown in FIG. 2(c). In the equivalent circuit 20b, a circuit 21 represented by a resistor Rb and a capacitor C2 is an equivalent circuit of the water molecules 11.

As shown in FIG. 2(c), when moisture (the water molecules 11) is(are) adsorbed on the insulating section 4, the resistor Rb and the capacitor C2 derived from the water molecules 11 are generated as shown in FIG. 2(d), and the impedance changes (decreases) by the resistor Rb and the capacitor C2. As a result, a current flow between the detection electrode 3 and the application electrode 2, and a voltage can be detected from the detection electrode 3. With such a detection manner of the moisture in a breath that uses the change in impedance of the moisture detection element 1 caused by deposition of moisture (the water molecules 11) on the insulating section 4, the responsibility can be increased.

Incidentally, as shown in FIG. 1(b), the detection electrode 3 and the application electrode 2 each have a comb-teeth shape. The detection electrode 3 and the application electrode 2 are arranged with a gap therebetween on the insulating section 4 so that the comb-teeth of the detection electrode 3 and the comb-teeth of the application electrode 2 face each other while being mated with each other. This can increase the area of the moisture deposition portion (reaction site).

For example, the capacitance humidity sensor described in PTL 1 is intended to measure humidity in the air.

In contrast, the moisture detection element 1 of the embodiment is intended to detect a breath having a high humidity (mostly in the saturated state). Accordingly, the moisture detection element 1 is not intended to measure the moisture content in the air but to simply detect a high humidity air (breath).

In the moisture detection element 1 of the embodiment, as shown in FIG. 1, the insulating section 4 is interposed between the detection electrode 3 and the application electrode 2. As shown in FIG. 2(c), when the water molecules 11 contained in a breath are adsorbed on the insulating section 4, a current is allowed to flow with the water molecules 11 as a path. This results in detection of an output voltage by the detection electrode 3. Accordingly, the moisture detection element 1 of the embodiment is only required to include the insulating section 4 having an area where the water molecules 11 can be adsorbed, thereby achieving the size reduction of the moisture detection element.

In addition, before moisture (the water molecules 11) is(are) adsorbed on the insulating section 4, the output voltage is almost 0, whereas after moisture (the water molecules 11) is(are) adsorbed, the output voltage can be almost Vi (applied voltage). This can achieve an excellent S/N (Signal/Noise) ratio.

Incidentally, in the moisture detection element 1, the surface of the insulating section 4 has a projections-and-depressions structure as described above. Such projections and depressions on the surface of the insulating section 4 can increase the surface area of the insulating section 4. That is, such projections and depressions on the surface of the insulating section 4 allows for deposition of more water molecules 11 to increase the output voltage, resulting in the high sensitivity.

Furthermore, the insulating section 4 which is, at least at the surface thereof, made of a highly hydrophilic oxide (metal oxide) can facilitate the moisture deposition.

(Size Reduction)

FIG. 3 is a view for comparing the size of a moisture detection element in a comparative example with that of the moisture detection element of the embodiment. FIG. 1 will be referred to as needed.

An ion detection sensor A which is a moisture detection element in the comparative example utilizes the ion detection device described in PTL 2.

Incidentally, the ratio of the size of the ion detection sensor A to that of the moisture detection element 1 according to the embodiment in FIG. 3 is the same as the actual ratio. FIG. 3 shows an example in which the moisture detection element 1 of the embodiment is set in a universal serial bus (USB) terminal for evaluation.

A voltage is applied to a power source application electrode A4, and a counter electrode A5 detects the amount of the ionized water cluster. In this manner, the amount of the water cluster in a sample (breath) that is introduced from a breath introduction port A1 into a housing of the ion detection sensor A and remains in the housing of the ion detection sensor A is detected. Then, the breath remaining in the housing of the ion detection sensor A is discharged by an exhaust fan section A3.

As seen above, since the ion detection sensor A has a configuration in which an ion detection sensor is housed in a case, an evacuation is needed between the detection of one breath and the introduction of the next breath. Accordingly, the ion detection sensor A is required to include the exhaust fan section A3 for discharging a breath after detection of the breath.

As shown in FIG. 3, the size of the moisture detection element 1 of the embodiment can be reduced to 1/10 or smaller as compared with the ion detection sensor A of the comparative example. This is because the moisture detection element 1 of the embodiment measures a voltage between the application electrode 2 and the detection electrode 3 generated by a current flowing with the water molecules 11 (see FIG. 2) adsorbed on the insulating section 4 as a path, and thus a breath does not have to remain, thereby requiring no housing.

As seen above, the size reduction realized in the moisture detection element 1 of the embodiment makes it possible to use the moisture detection element 1 in a form according to various use purposes, for example, a built-in form in a mobile device, thereby widening its application range.

Since the moisture detection element 1 of the embodiment detects a current generated with moisture (the water molecules 11) adsorbed on the insulating section 4 as a path, even a very small amount of moisture can be detected. Since only a small amount of moisture is needed for the detection, the moisture immediately (in a few seconds or so) vaporizes after detection, and therefore, discharge of a breath in a housing is not needed unlike in the ion detection sensor A. Accordingly, the moisture detection element 1 of the embodiment is not required to include the exhaust fan section A3 for discharging breath, and thus can achieve greater size reduction than the ion detection sensor A.

Since the ion detection sensor A has to discharge a breath, it is difficult to perform the next measurement immediately after completion of one measurement. Incidentally, also in the capacitance humidity sensor described in PTL 1, it takes a certain time to eliminate moisture from the moisture sensitive film to return to the normal state, and therefore it is difficult to perform the next measurement immediately after completion of one measurement. As described above, the ion detection sensor A and the capacitance humidity sensor described in PTL 1 are not suitable for a use purpose involving frequently repeated use.

In contrast, in the moisture detection element 1 of the embodiment, since moisture vaporizes immediately after detection as described above, the next measurement can be performed immediately after completion of one measurement.

The moisture detection element 1 of the embodiment uses an AC voltage as an applied voltage as shown in FIG. 1. This allows the moisture detection element 1 of the embodiment to achieve speed enhancement. In other words, when a DC voltage is used as an applied voltage, a delay occurs in the voltage rising by the capacitor C1 and C2 components in the equivalent circuit 20 shown in FIG. 2(d), resulting in a delay in the detection. In contrast, when an AC voltage is used as an applied voltage, the influence of the capacitor C1 and C2 components is small and thus the delay in detection is reduced. In particular, when an AC voltage having a frequency of several tens of hertz or higher is used as an applied voltage, high-speed detection can be achieved.

Furthermore, in the moisture detection element 1 of the embodiment, no current flows and thus no power is consumed before introduction of a breath. In contrast, in the capacitance humidity sensor described in PTL 1, even when no breath is introduced, a current has to flow in the moisture sensitive film. As seen above, the moisture detection element 1 of the embodiment can achieve power saving. Accordingly, the moisture detection element 1 of the embodiment is suitable for a mobile use.

In the moisture detection element 1 of the embodiment, a current flowing via moisture (the water molecules 11) adsorbed on the insulating section 4 may be approximately several nano-amperes (nA) or several pico-amperes (pA). Accordingly, the moisture detection element 1 of the embodiment can achieve power saving. This is because the output voltage Vo is almost 0 before moisture deposition and therefore such a small current as approximately several nano-amperes or several pico-amperes can be detected. In contrast, in the capacitance humidity sensor described in PTL 1, a current has to flow in the moisture sensitive film even when no breath is introduced as described above. Accordingly, for the output voltage, a larger current is required to flow than the current of the time where no breath is introduced.

Since the capacitance humidity sensor described in PTL 1 detects the humidity by adsorption of water vapor into the moisture sensitive film, it takes a time for detection, making it difficult to detect the moisture while a human exhales a breath. This is because the capacitance humidity sensor described in PTL 1 is intended to accurately measure the humidity.

In contrast, since the moisture detection element 1 of the embodiment detects a voltage generated by a current flowing with moisture (the water molecules 11) adsorbed on the insulating section 4 as a path, the detection time can be considerably reduced and thus moisture can be detected while the subject exhales a breath. In other words, the moisture detection element 1 of the embodiment is not intended to accurately measure humidity unlike in the capacitance humidity sensor described in PTL 1, but intended to determine simply whether or not a sufficient amount of moisture is contained in the air introduced.

(Output Characteristics)

FIG. 4 is a graph showing comparison between the output of the ion detection sensor in the comparative example and that of the moisture detection element of the embodiment. Incidentally, in FIG. 4, the ion detection sensor in the comparative example is the ion detection sensor described in PTL 2.

In FIG. 4, the vertical axis represents the output voltage and the horizontal axis represents the time (sec).

In FIG. 4, a wave 51 (solid line) represents the output of the ion detection sensor described in PTL 2 and a wave 52 (dotted line) represents the output of the moisture detection element 1 of the embodiment.

As shown in FIG. 4, the output (wave 52) of the moisture detection element 1 of the embodiment is remarkably larger as compared with the output (wave 51) of the ion detection sensor described in PTL 2.

As seen above, the ion detection sensor described in PTL 2 has a small output and the output has to be amplified by an amplifier or the like. A power thus needed for the amplifier leads to a large power consumption.

In contrast, as shown in FIG. 4, the moisture detection element 1 of the embodiment can output a value one or more digits larger than that of the ion detection sensor described in PTL 2.

Because of the capability of outputting such a large value, the moisture detection element 1 of the embodiment requires no amplifier and can realize power saving and size reduction.

FIG. 5 is graphs for explaining characteristics of the moisture detection element of the embodiment in which (a) shows a frequency characteristic, (b) shows a characteristic with respect to the electrode length, (c) shows a response characteristic, and (d) shows a response characteristic of a known technique as a comparative example.

First, in FIG. 5(a), the horizontal axis represents the frequency (Hz) of the applied AC voltage and the vertical axis represents the ratio (Vo/Vi) of the output voltage (Vo) to the applied voltage (Vi).

As shown in FIG. 5(a), the output voltage Vo is slightly smaller than the applied voltage Vi due to influence of an impedance derived from the water molecules 11 (see FIG. 2) and the like, but applied voltage (Vi)≈output voltage (Vo) is stably satisfied (Vo/Vi≈1) in almost all frequencies.

In FIG. 5(b), the horizontal axis represents the whole length W of a detection portion in the detection electrode 3 and the vertical axis represents the S/N ratio of the output voltage. Here, the whole length W of the detection portion is obtained by multiplying the length L of the detection portion of the detection electrode 3 shown in FIG. 1 by N-1 wherein N represents the number of the comb-teeth in the application electrode 2 or the detection electrode 3.

As shown in FIG. 5(b), as the whole length W of the detection portion increases, the S/N ratio increases. This is because, as the whole length W of the detection portion increases, the area for detecting the output voltage Vo increases and accordingly noise is relatively reduced. As seen above, when the shapes of the application electrode 2 and the detection electrode 3 are made into comb-teeth shapes and the application electrode 2 and the detection electrode 3 are arranged with a gap therebetween so that the comb-teeth portions are mated with each other, the whole length W of the detection portion can be increased and a high S/N ratio can be realized.

In FIG. 5(c), the horizontal axis represents the time (sec) and the vertical axis represents the ratio (Vo/Vi) of the output voltage (Vo) to the applied voltage (Vi).

In contrast, for example, in FIG. 5(d) which shows a response characteristic of a technique of a comparative example (a technique of measuring humidity using the moisture sensitive film as described PTL 1), the horizontal axis represents the time and the vertical axis represents the humidity based on the ion current flowing in the moisture sensitive film. Incidentally, in the moisture detection element 1 in the embodiment, since an AC voltage is output, the practical output wave is in a wave shape as shown in FIG. 18 which is described later. However, for easy comparison with FIG. 5(d), the wave is shown as if it is a direct current in FIG. 5(c). Accordingly, FIG. 5(c) may be taken as the variation of the peak value of the output AC voltage.

Incidentally, in FIG. 5(c), the time t1 is a time when the moisture detection element 1 determines that a breath introduction is started, and the time t2 is a time when the breath introduction is ended. The time t3 is a time when the output voltage Vi substantially returns to the state before the breath introduction.

In FIG. 5(d), the time t1a is the time when the device in the technique of the comparative example determines that a breath introduction is started, and time t2a is the time when the breath introduction is ended. In FIG. 5(d), the output voltage Vi has not still returned to the state before the breath introduction even when 5 seconds or more have elapsed after the breath introduction.

As compared with the comparative example shown in FIG. 5(d), the moisture detection element 1 of the embodiment shown in FIG. 5(c) has higher responsibility after the breath introduction.

This is because, in the moisture detection element 1 of the embodiment, as shown in FIG. 2(b) and FIG. 2(d), the detection electrode 3 detects the voltage by change in impedance due to the water molecules 11 adsorbed on the insulating section 4. As seen above, the moisture detection element 1 of the embodiment can achieve excellent responsibility.

Incidentally, the response time may be adjusted by adjustment of the gap between the comb-teeth of the application electrode 2 and the comb teeth of the detection electrode 3 shown in FIG. 1(b).

In FIG. 5(d), the time period from the start of the breath introduction to the end of the breath introduction is almost the same as in FIG. 5(c), but in FIG. 5(d), the humidity is far from 100% which is the actual breath humidity. Accordingly, in the comparative example, breath introduction has to be continued until the humidity becomes 100% which is the actual breath humidity. Accordingly, in the technique of the comparative example, it is difficult to achieve sufficient measurement in a few seconds during which a human exhales a breath in a natural manner.

In contrast, as shown in FIG. 5(c), in the moisture detection element 1 of the embodiment, the graph more sharply rises than in FIG. 5(d) and reaches the peak in a shorter time period (approximately, less than 1 second). In other words, the moisture detection element 1 of the embodiment has higher responsibility than the technique of the comparative example. In addition, the output voltage Vo at the peak top is almost the same as the applied voltage Vi (Vo/Vi≈1).

As seen above, the moisture detection element 1 of the embodiment can sufficiently achieve a measurement of a breath in a short time period.

Furthermore, it can be seen that, also after the breath introduction, the moisture detection element 1 of the embodiment shown in FIG. 5(c) returns to the state before the breath introduction in a shorter time period as compared with the comparative example shown in FIG. 5(d). This is because the technique of the comparative example is based on the ion current flowing through the moisture sensitive film due to the adsorption of moisture on the moisture sensitive film, and therefore a delay occurs in the reaction to return to the state before the breath introduction.

In contrast, the moisture detection element 1 of the embodiment detects moisture based on the current flow due to the moisture (the water molecules 11) adsorbed on the insulating section 4 as described above. Accordingly, response can be made in a short period of time after the breath introduction. In addition, since the amount of moisture adsorbed on the insulating section 4 is very small, the moisture vaporizes immediately after the breath introduction.

As shown in FIG. 5(d), the speed for returning to the state before the breath introduction is low in the comparative example. Accordingly, in the technique of the comparative example, it takes approximately 30 seconds to 1 minute to return to a state where the next measurement can be started.

In contrast, in the moisture detection element 1 of the embodiment, as shown in FIG. 5(c), the time period from the start of a breath introduction to the time when the output voltage Vi gets back to the state before the breath introduction is approximately 3 seconds. As seen above, in the moisture detection element 1 of the embodiment, when a breath introduction is ended, the moisture detection element 1 can immediately return to the state before the breath introduction, and therefore the next inspection can be started soon.

(Projections-and-Depressions Structure)

FIG. 6 shows an example of a low temperature type and a high temperature type moisture detection elements according to the embodiment in which (a) is a top view of the moisture detection element, (b) is a schematic view illustrating the principle of a low temperature type moisture detection element, and (c) is a schematic view illustrating the principle of a high temperature type moisture detection element.

In the moisture detection element 1 of the embodiment, the insulating section 4 has a projections-and-depressions structure as described above.

As shown in FIG. 6, the projections-and-depressions structure in the low temperature type which is used in a low temperature environment (under an environment of a prescribed temperature or lower) can be distinguished from the projections-and-depressions structure of the high temperature type which is used in a high temperature environment (under an environment of a prescribed temperature or higher).

In other words, as shown in FIG. 6(b), the low temperature type moisture detection element 1a has smaller projections and depressions in the insulating section 4a than the high temperature type moisture detection element 1b. Conversely, as shown in FIG. 6(c), the high temperature type has larger projections and depressions in the insulating section 4b than the low temperature type.

At a higher temperature, the amount of saturated water vapor is larger and breath humidity (relative humidity) is lower. Accordingly, in the high temperature type, the magnitude of the projections and depressions in the insulating section 4b is increased to facilitate the deposition of moisture (the water molecules 11 (see FIG. 2)). In this manner, the moisture detection element 1b that appropriately acts even under a high temperature environment with a low breath humidity can be provided.

Conversely, at a lower temperature, the amount of saturated water vapor is smaller and thus the breath humidity (relative humidity) is higher. In such a state, if the projections and depressions in the insulating section 4 are large as in the high temperature type, an excessive amount of moisture (the water molecules 11) is(are) adsorbed. Accordingly, in the low temperature type moisture detection element 1a, the magnitude of the projections and depressions in the insulating section 4a is decreased to suppress the deposition of moisture (the water molecules 11) as compared with the high temperature type moisture detection element 1b. In this manner, the moisture detection element 1a that appropriately acts even under a low temperature environment with a high breath humidity can be provided.

As shown in FIG. 6(a), an AC voltage is applied from the AC power source 5 to the low temperature type moisture detection element 1a and the high temperature type moisture detection element 1b. With such a configuration, the moisture detection element 1 that can be used both under a low temperature environment and under a high temperature environment can be provided.

Incidentally, in the example of FIG. 6, there are two types in the magnitude of the projections and depressions in the insulating section 4 for the low temperature type and the high temperature type, but there may be three types or more. That is, by increasing the magnitude of the projections and depressions from the low temperature type to the high temperature type, there may be provided the moisture detection element 1 including the insulating section 4 that is suitable for an intermediate temperature between the low temperature type and the high temperature type. Incidentally, the low temperature type moisture detection element 1a and the high temperature type moisture detection element 1b may be switchable depending on the environmental temperature.

Here, the projections and depressions in the insulating section 4 may be in a mountain shape as shown in FIG. 6 or in a protrusion shape as shown in FIG. 7. Alternatively, the projections and depressions in the insulating section 4 may be formed in a shape other than the mountain shape and protrusion shape, such as a random shape.

FIG. 7 shows another example of the low temperature type and high temperature type moisture detection elements according to the embodiment in which (a) is a top view of the moisture detection element, (b) is a schematic view illustrating the principle of a low temperature type moisture detection element, and (c) is a schematic view illustrating the principle of a high temperature type moisture detection element.

Incidentally, as shown in FIG. 7(a), an applied voltage (AC voltage) is applied from the AC power source 5 to a low temperature type moisture detection element 1c including the insulating section 4c having projections and depressions of a small protrusion shape illustrated in FIG. 7(b) and a high temperature type moisture detection element 1d including the insulating section 4d having projections and depressions of a large protrusion shape illustrated in FIG. 7(c).

(Formation Method of Projections-and-Depressions Structure)

FIG. 8 shows a method for forming the projections-and-depressions structure in the insulating section in which (a) shows a processing treatment, (b) shows an amorphous treatment, and (c) shows a printing treatment.

The projections and depressions in the insulating section 4 may be formed by a processing treatment in which the insulating section 4 is carved from the state shown by the dotted line as shown in FIG. 8(a). The insulating section 4 may be formed by an amorphous treatment as shown in FIG. 8(b). Alternatively, the insulating section 4 may be formed by a printing treatment in which the projections and depressions are printed on a flat substrate as shown in FIG. 8(c). Incidentally, the insulating section 4 formed by an amorphous treatment shown in FIG. 8(b) is apparently has a smooth surface, but projections and depressions in a crystal unit exist in practice.

Modification Example

FIG. 9 is a diagram showing another example of the moisture detection element 1 of the embodiment. Incidentally, identical signs are given in the same configuration as in FIG. 1 to omit the explanation.

In the moisture detection element 1C(1) shown in FIG. 9, the application electrode 2a(2) and the detection electrode 3a(3) are each in a spiral shape. As is seen in this case, the detection electrode 3 and the application electrode 2 may not be in a comb-teeth shape as shown in FIG. 1.

[Breath Sensor]

Next, a breath sensor using the moisture detection element 1 will be explained.

(Planar Arrangement Structure)

FIG. 10 shows an example of a breath sensor having a planar arrangement structure. In a breath sensor (gas detection device) 100a(100) having a planar arrangement structure shown in FIG. 10, the moisture detection element 1 is disposed at the center of a circuit board having a planar structure, and compact gas sensors (gas detection sections) 101 are arranged around the moisture detection element 1. The moisture detection element 1 is any one of those shown in FIG. 1, FIG. 6, FIG. 7, and FIG. 9.

The gas sensors 101 arranged around the moisture detection element 1 are configured to include a gas sensor for carbon monoxide 101a, a gas sensor for nitrogen monoxide 101b, a gas sensor for alcohol 101c, a gas sensor for acetaldehyde 101d, a gas sensor for acetone 101e, a gas sensor for hydrogen 101f, and the like. Incidentally, although alcohol includes various kinds, this example is explained using ethanol as an example.

Incidentally, the gas sensor for carbon monoxide 101a can detect the presence or absence of smoking, the gas sensor for nitrogen monoxide 101b can detect the presence or absence of asthma, the gas sensor for alcohol (ethanol) 101c can detect the presence or absence of alcohol drinking (the presence or absence of alcohol in a breath), the gas sensor for acetaldehyde 101*d* can detect the presence or absence of sick due to alcohol drinking (acetaldehyde is a metabolite of alcohol), the gas sensor for acetone 101*e* can detect the presence or absence of diabetes, and the gas sensor for hydrogen 101*f* can detect the presence or absence of abnormality in digestive organs. Incidentally, as used herein, the "presence or absence" means whether or not a predetermined level or more of the component is contained in the breath.

FIG. 10 has a configuration including 6 kinds of gas sensors 101, but not all the kinds are necessarily provided, and a configuration including one or a few kinds of gas sensors 101 may be adopted depending on the purpose. Alternatively, a configuration in which the gas sensors 101 to be used can be switched depending on the purpose may be adopted. Furthermore, the gas sensor is not limited to the gas sensors 101 used in the example shown in FIG. 10, and, for example, the gas sensor 101 for carbon dioxide or the like may be provided.

(Coaxial Structure)

FIG. 11 shows examples of a breath sensor having a coaxial structure in which (a) is an external perspective view of a breath sensor, (b) is a top view of the breath sensor, (c) illustrates a structure of the substrate section, (d) illustrates a structure of a portion to which the gas sensors are mounted, and (e) shows another example of the mounting direction of the gas sensor.

As shown in FIG. 11(*a*) and FIG. 11(*b*), a rod-shaped application electrode 112(2) is disposed at the center of a breath sensor 100*b*(100), and a cylindrical detection electrode 113(3) is disposed around the application electrode 112. The application electrode 112 and the detection electrode 113 are connected via one or more (four in the example of FIG. 11) tabular substrate sections 120. As shown in FIG. 11(*c*), the substrate section 120 includes an application electrode plate 122 connected to the rod-shaped application electrode 112 and the detection electrode plate 123 connected to the cylindrical detection electrode 113. The application electrode plate 122 and the detection electrode plate 123 each have a comb-teeth structure, and as with the application electrode 2 and the detection electrode 3 in FIG. 1(*b*), the application electrode plate 122 and the detection electrode plate 123 are placed with a gap therebetween so that the comb-teeth portions are mated with each other. In addition, an insulating section 124(4) is interposed between the application electrode plate 122 and the detection electrode plate 123. Such a configuration is the same as the configuration shown in FIG. 1, and hence a detailed description is omitted here.

A breath is introduced inside the cylindrical detection electrode 113, and moisture (the water molecules 11 (see FIG. 2)) in the breath is(are) adsorbed on the insulating section 124 in the substrate section 120. This allows a current to flow between the application electrode plate 122 and the detection electrode plate 123 in the substrate section 120 via the adsorbed moisture (the water molecules 11), whereby the moisture in the breath can be detected.

As shown in FIG. 11(*a*), various kinds of gas sensors 101*a* to 101*f*(101) are placed on the external side surface of the cylindrical detection electrode 113. Here, the gas sensors 101*a* to 101*f* are the same as the gas sensors 101*a* to 101*f* shown in FIG. 10. Incidentally, this example has a configuration including 6 kinds of gas sensors 101 here, but not all the kinds are necessarily provided, and a configuration including one or a few kinds of gas sensors 101 may be adopted depending on the purpose. Alternatively, a configuration in which the gas sensors 101 to be used can be switched depending on the purpose may be adopted. Furthermore, the gas sensor is not limited to the gas sensors 101 used in the example shown in FIG. 10, and the gas sensor 101 for carbon dioxide or the like may be provided.

FIG. 11(*d*) shows the detection electrode 113 in which the gas sensors 101 is removed from the positions at which the gas sensors 101 are to be mounted.

As shown in FIG. 11(*d*), in the cylindrical detection electrode 113, through holes 131 are provided at the positions corresponding to the positions at which the gas sensors 101 are to be mounted. A breath introduced inside the detection electrode 113 tends to go toward the outside from the through holes 131. At this time, the gas sensors 101 provided in the through holes 131 detect the gas components contained in the breath.

With the configuration as shown in FIG. 11(*a*) to (*d*), since the breath sensor 201 itself can have a cylindrical shape, the shape of the space to be secured can be varied.

Incidentally, a plurality of gas sensors 101 are arranged in an axial direction of the breath sensor 100*b*, but as shown in FIG. 11(*e*), a breath sensor 100*c* in which various kinds of the gas sensors 101 are arranged in the peripheral direction of the detection electrode 113 may be adopted. Incidentally, the gas sensors 101 in FIG. 11(*e*) are the gas sensors 101*a* to 101*f* in FIG. 11(*a*). In this case, in the cylindrical detection electrode 113, through holes 131 are provided at the position corresponding to the gas sensors 101 as with the case of FIG. 11(*d*). With the configuration as shown in FIG. 11(*e*), the length in the axial direction of the breath sensor 100*c* can be reduced.

As shown in FIG. 10 and FIG. 11, by combining the moisture detection element 1 and the gas sensors 101, moisture in a breath can be detected. This enables detection of impersonation by introduction of an air other than breath into the breath sensor 100.

Incidentally, the gas sensor 101 used in the embodiment is desirably made as small as possible.

[Breath Inspection Device]

Next, with reference to FIG. 12 and FIG. 13, an example of a breath inspection device including the breath sensor 100 according to the embodiment will be described.

(Mobile Type)

FIG. 12 shows an example of a mobile type breath inspection device. A breath inspection device 201*a*(201) shown in FIG. 12 has, for example, a business card size.

The breath inspection device 201*a* has a breath introduction port 202*a* and a display section 203. The breath sensor 100 (see FIG. 10 and FIG. 11) is built in the breath inspection device 201*a*.

That is, for a breath introduced from the breath introduction port 202*a* to the inside of the breath inspection device 201*a*, detections for breath and gas are performed by the breath sensor 100 therein. Then, the inspection results by the breath inspection device 201*a* are displayed on the display section 203.

The possibility of the size reduction of the moisture detection element 1 leads to the possibility of the size reduction of the breath inspection device 201*a*. As a result of such a size reduction of the breath inspection device 201*a*, the breath inspection device 201*a* can be used for domestic use, or can be mounted on a bicycle, thereby providing a healthcare product used in an easy manner.

Incidentally, the breath sensor 100 built in the breath inspection device 201*a* is desirably the breath sensor 100*a* shown in FIG. 10, but may be the breath sensor 100*b* shown in FIG. 11.

When the breath sensor 100b shown in FIG. 11 is used, the breath introduction port 202a may be directly connected to an end of the breath sensor 100b shown in FIG. 11. With such a configuration, the size of the breath inspection device 201 may be further reduced.

(Steering Wheel)

FIG. 13 shows an example of a breath inspection device incorporated in a steering wheel.

In the breath inspection device 201b(201) shown in FIG. 13, the breath sensor 100 is incorporated inside the steering wheel 211. On the ring portion of the steering wheel 211, the breath introduction port 202b is provided as shown in FIG. 13. The moisture and gas in a breath introduced from the breath introduction port 202b to the inside of the ring portion of the steering wheel 211 are detected by the breath sensor 100 provided inside the ring portion.

The breath sensor 100 provided inside the steering wheel 211 in FIG. 13 is preferably the breath sensor 100b shown in FIG. 11, but may be the breath sensor 100a shown in FIG. 10.

When the breath sensor 100b shown in FIG. 11 is used, the end portions of the breath sensor 100b may be connected to each other into a ring form, making it possible to use the breath sensor 100b itself as the ring portion of the steering wheel 211. This can integrate the steering wheel 211 and the breath sensor 100. As a result, it is not required to provide the breath sensor 100 as a separate device, eliminating the need to secure a space for placement of the breath sensor 100.

When the gas sensors 101 are arranged around the moisture detection element 1 as shown in FIG. 10 and FIG. 11, the moisture detection element 1 can determine whether or not the amount of the moisture in a breath introduced is sufficient, thereby confirming whether or not the introduced air is truly a breath while measuring various gases in the breath.

[Breath Inspection System]

FIG. 14 shows an example of functional blocks of the breath inspection system according to the embodiment.

A breath inspection system Z includes a breath detection device 300, an analysis device 500, a transmission device 601, and a storage device 602.

The breath detection device 300 includes a breath sensor 100 and a measurement control device 400. The breath sensor 100 includes the moisture detection element 1 and the gas sensor 101. The breath sensor 100 has been explained in FIG. 10 and FIG. 11 and hence the explanation is omitted here.

The measurement control device 400 converts the frequency of the AC power source 5 and outputs the resultant.

The breath detection device 300 converts analog signals input from the moisture detection element 1 and the gas sensor 101 into digital signals by analog/digital (A/D) converters 301a and 301b and outputs the resultant signals into the analysis device 500.

The analysis device 500 acquires an output voltage from the moisture detection element 1 in the breath sensor 100, and acquires a detection signal from the gas sensor 101. Then, the analysis device 500 analyzes the gas content in the breath based on the output voltage acquired from the moisture detection element 1, the detection signal acquired from the gas sensor 101, and the like. Incidentally, in the embodiment, the analysis device 500 acquires the output voltage and the detection signal from the breath sensor 100, but the present invention is not limited thereto, and the measurement control device 400 may acquire the output voltage and the detection signal from the breath sensor 100 to send the acquired output voltage and detection signal to the analysis device 500.

The storage device 602 is a database server or the like, and holds the output voltage acquired by the analysis device 500 from the moisture detection element 1 or the detection signal acquired from the gas sensor 101 along with the inspection time, and holds analysis results by the analysis device 500.

The transmission device 601 informs a central information center (not shown) of the analysis results (information about the state of the driver and the like) given by the analysis device 500.

(Measurement Control Device)

FIG. 15 is a functional block diagram showing a configuration example of a measurement control device according to the embodiment.

The measurement control device 400 includes a memory 401, a central processing unit (CPU) 402, an input device 403, an AC/AC invertor circuit 404, an AC terminal 405, an AC/DC converter circuit 406, and a DC terminal 407.

In the memory 401, a control section 411 embodies a program by allowing the CPU 402 to execute the program.

The control section 411 sends an instruction to the AC/AC invertor circuit 404 and the AC/DC converter circuit 406 based on information input via the input device 403.

The AC/AC invertor circuit 404 converts the frequency and voltage of an AC voltage input from the AC power source 5 based on the instruction sent from the control section 411 and outputs the resultant to the AC terminal 405. The AC terminal 405 is connected to the moisture detection element 1.

The AC/DC converter circuit 406 converts the voltage of the AC voltage input from the AC power source 5 based on the instruction sent from the control section 411, and further converts the AC current to a DC current and output the DC current to the DC terminal 407. The DC terminal 407 is connected to the gas sensor 101.

Incidentally, the configuration of the measurement control device 400 shown in FIG. 15 is one example, and the present invention is not limited to the configuration shown in FIG. 15. For example, an AC signal (AC voltage) may be generated using a quartz oscillator.

(Analysis Device)

FIG. 16 is a functional block diagram showing a configuration example of the analysis device according to the embodiment.

The analysis device 500 is, for example, a personal computer (PC), and includes a memory 501, a CPU 502, a transmission/reception device 503, a display device 504, a storage device 505 such as a hard disk drive (HDD), and the like.

A program stored in the storage device 505 is loaded into the memory 501, and the CPU 502 executes the program to embody a processing section 511, and a moisture measurement processing section 512, a gas measurement processing section 513, and the determination processing section 514 which constitutes the processing section 511.

The moisture measurement processing section 512 performs processing about a measurement of moisture contained in a breath based on the signal sent from the moisture detection element 1.

The gas measurement processing section 513 performs processing about a measurement of a gas of various kinds contained in the breath based on the signal sent from the gas sensor 101.

The determination processing section 514 determines whether or not the subject has drunk alcohol based on the measurement result of the gas measurement processing section 513.

Incidentally, when the measurement of a gas is not performed in the breath inspection system Z, the gas measurement processing section 513 can be omitted.

Incidentally, in the breath inspection system Z shown in FIG. 14, the breath detection device 300, the analysis device 500, the transmission device 601, and the storage device 602 are separate devices, but the present invention is not limited thereto, and at least two of the breath detection device 300, the analysis device 500, the transmission device 601, and the storage device 602 may be integrated into one device.

For example, the breath inspection device 201a shown in FIG. 12 may be provided with all of the breath detection device 300, the analysis device 500, the transmission device 601, and the storage device 602.

The breath inspection device 201b shown in FIG. 13 may be provided with only the breath detection device 300, and the analysis device 500, the transmission device 601, and the storage device 602 may be provided in another place in the vehicle.

[Flowchart]

Next, a processing procedure of the breath inspection system Z according to the embodiment will be described with reference to FIGS. 17 to 21. FIGS. 13 to 16 will be referred to as needed.

(Breath Detection Processing)

FIG. 17 is a flowchart showing a procedure of breath detection processing according to the embodiment.

First, a user turns on a power source of the breath inspection system Z (S101), whereby an AC voltage (applied voltage) is applied to the application electrode 2 (S102). Incidentally, the applied AC voltage is output from the AC terminal 405 of the measurement control device 400.

Then, the subject introduces a breath into a breath introduction port, whereby a breath introduction is started (S103).

Then, the moisture measurement processing section 512 starts a measurement of the output voltage Vo from the moisture detection element 1, whereby a moisture measurement is started (S104). In this time, the moisture measurement processing section 512 subtracts the voltage value during the time from time 0 to time t0 as an offset value from the output voltage at this time to calculate the output voltage Vo.

Then, the moisture measurement processing section 512 determines whether the output voltage Vo from the moisture detection element 1 is equal to or more than a first threshold Vth1 (S111).

As a result of Step S111, when the output voltage Vo from the moisture detection element 1 is less than the first threshold Vth1 (S111→No), the moisture measurement processing section 512 determines that the breath is short in strength and allows the subject to continue breath introduction (S112). Then, the moisture measurement processing section 512 returns the processing to Step S111.

As a result of Step S111, when the output voltage Vo is equal to or more than the first threshold Vth1 (S111→Yes), the moisture measurement processing section 512 determines whether the output voltage Vo from the moisture detection element 1 is equal to or more than a second threshold Vth2 (S113). Incidentally, the first threshold Vth1<the second threshold Vth2 is satisfied. In addition, the output voltage Vo is an AC voltage in practice, and the moisture measurement processing section 512 determines "whether the output voltage Vo is equal to or more than the second threshold Vth2" according to whether the number of times when the output voltage peak is equal to or more than the second threshold Vth2 exceeds a predetermined number. This will be explained later As a result of Step S113, when the output voltage Vo is less than the second threshold Vth2 (S113→No), the moisture measurement processing section 512 determines that the breath is short in strength and allows the subject to continue breath introduction (S114). Then, the moisture measurement processing section 512 returns the processing to Step S113.

As a result of Step S113, when the output voltage Vo is equal to or more than the second threshold Vth2 (S113→Yes), the moisture measurement processing section 512 determines that the breath is sufficient in strength (S121). Then, the subject ends the breath introduction (S122). At this time, the breath detection device 300 informs the subject of the matter that the breath introduction is to be ended by a buzzer, a voice, or a display on a screen.

FIG. 18 is a graph showing a temporal variation of the output voltage.

In FIG. 18, the horizontal axis represents the time (sec) and the vertical axis represents the output voltage (in arbitrary unit). Incidentally, in FIG. 5(c) and FIG. 18, the times for each event are different because data of different tests are used, but the graphs show almost the same characteristics.

First, when the subject starts a breath introduction at time t0 (Step S103 in FIG. 17), the output voltage begins to increase, and the output voltage exceeds the first threshold Vth1 at time t11 (Step S111 in FIG. 17; Yes). The time t0 corresponds to the time t1 in FIG. 5(c).

Then, the output voltage continues to increase, and the number of the output voltage peaks exceeds 15 so that the output voltage exceeds the second threshold Vth2 at time t12 (Step S113 in FIG. 17; Yes). The number of times at this time may be arbitrary set. Depending on the frequency, this number is set to the peak number corresponding to approximately 1 second to 3 seconds after the output voltage exceeds the first threshold Vth1.

Incidentally, the second threshold Vth2 is a sufficient output voltage to confirm that moisture is contained in the introduced air (breath).

Then, the subject ends the breath introduction at time t13 (Step S122 in FIG. 17). Incidentally, the time t13 corresponds to the time t2 in FIG. 5(c).

(Gas Detection Processing)

FIG. 19 and FIG. 20 are flowcharts showing a procedure of a gas detection processing according to the embodiment. In the processing shown in FIG. 19 and FIG. 20, the processing shown in FIG. 17 is used. Incidentally, FIG. 19 and FIG. 20 show the case where the gas to be detected is alcohol, but a gas other than alcohol can be detected by the same procedure. In a practical alcohol detection, besides alcohol, acetaldehyde which is a metabolite and hydrogen which is contained in breath at a high concentration of about 10 ppm are set as measurement subjects, and the gas concentration of alcohol is calculated based on the gas concentrations of alcohol, acetaldehyde, and hydrogen. In this way, it is possible to calculate an accurate gas concentration of alcohol. This procedure is also used here, and the gas sensor for alcohol 101c, the gas sensor for acetaldehyde 101d, and the gas sensor for hydrogen 101f are used as the gas sensors 101. Hereinunder, the respective gas sensors 101 of the gas sensor for alcohol 101c, the gas sensor for acetaldehyde 101d, and the gas sensor for hydrogen 101f are referred to as gas sensors 101c, 101d, and 101f. In the flowcharts of FIG. 19 and FIG. 20, the same step numbers are assigned to the same processing as in FIG. 17.

First, a user turns on the power source of the breath inspection system Z (S101 in FIG. 19), whereby an AC voltage is applied to the application electrode 2 (S102). Incidentally, the applied AC voltage is output from the AC terminal 405 of the measurement control device 400.

Then, the subject introduces a breath into the breath introduction port, whereby breath introduction is started (S103).

Then, the moisture measurement processing section 512 starts a measurement of the output voltage Vo from the moisture detection element 1, whereby a moisture measurement is started (S104). At this time, the moisture measurement processing section 512 subtracts the voltage value during the time from time 0 to time t0 as an offset value from the output voltage at this time to calculate the output voltage Vo.

Then, the moisture measurement processing section 512 determines whether the output voltage Vo from the moisture detection element 1 is equal to or more than the first threshold Vth1 (S111).

As a result of Step S111, when the output voltage Vo is less than the first threshold Vth1 (S111→No), the moisture measurement processing section 512 determines that the breath is short in strength and allows the subject to continue the breath introduction (S112). Then, the processing section 511 returns the processing to Step S111.

As a result of Step S111, when the output voltage Vo is equal to or more than the first threshold Vth1 (S111→Yes), the gas measurement processing section 513 starts an output measurement (gas measurement) from the gas sensors 101c, 101d, and 101f (S201).

Then, the moisture measurement processing section 512 determines whether the output voltage Vo from the moisture detection element 1 is equal to or more than the second threshold Vth2 (S113). The determination method of whether the output voltage Vo is equal to or more than the second threshold Vth2 is the same as in Step S113 in FIG. 17.

As a result of Step S113, when the output voltage Vo is less than the second threshold Vth2 (S113→No), the moisture measurement processing section 512 determines that the breath is short in strength and allows the subject to continue the breath introduction (S114). Then, the moisture measurement processing section 512 returns the processing to Step S113.

As a result of Step S113, when the output voltage Vo is equal to or more than the second threshold Vth2 (S113 Yes), the moisture measurement processing section 512 determines that the breath is sufficient in strength (S121) so that the processing section 511 ends the breath introduction (S122) and the gas measurement processing section 513 ends the output measurement (gas measurement) from gas sensors 101c, 101d, and 101f (S211).

Then, the gas measurement processing section 513 calculates the saturated output signals (gas saturated output signals) of the gas sensors 101c, 101d, and 101f based on the output curves from the beginning of the output to the ending of the output from the gas sensors 101c, 101d, and 101f (S221).

Furthermore, the gas measurement processing section 513 calculates the respective gas concentrations (saturated gas concentrations) of alcohol, acetaldehyde, and hydrogen in the saturated state based on the respective gas saturated output signals of alcohol, acetaldehyde and hydrogen calculated in Step S221 by a differential evolution method (S222). Such a manner of calculation of a saturated gas concentration of a certain gas based on plural saturated gas concentrations using a differential evolution method enables accurate calculation of the saturated gas concentration.

Then, the determination processing section 514 determines whether the saturated gas concentration of alcohol (alcohol concentration) among the saturated gas concentrations calculated in Step S222 is equal to or more than a reference value (S223 in FIG. 20).

As a result of Step S223, when the saturated gas concentration of alcohol (alcohol concentration) calculated in Step S222 is less than the reference value (S223→No), the determination processing section 514 determines that the subject has not drunk alcohol (S224).

As a result of Step S223, when the saturated gas concentration of alcohol (alcohol concentration) calculated in Step S222 is equal to or more than the reference value (S223→Yes), the determination processing section 514 determines that the subject has drunk alcohol (S225).

FIG. 21 is a graph showing a temporal change of the output signal output from the gas sensor. In FIG. 21, the vertical axis represents the output signal (V) and the horizontal axis represents the time (sec).

The time t11 in FIG. 21 corresponds to the time t11 in FIG. 18. That is, in FIG. 21, the output voltage from the moisture detection element 1 exceeds Vth1 at time t11. The gas measurement processing section 513 starts the gas measurement at time t11 when the output voltage from a moisture detection element 1 exceeds Vth1 (Step S201 in FIG. 19). Incidentally, since the gas sensor 101 begins to react before detecting the breath introduction, the time t11 is on the positive side of the origin.

The time t12 in FIG. 21 corresponds to the time t12 in FIG. 18. That is, in FIG. 21, the output signal reaches S1 and the output voltage from the moisture detection element 1 exceeds Vth2 at time t12. Then, when the gas measurement processing section 513 completes the gas measurement at time t12 (S211 in FIG. 19), the gas measurement processing section 513 estimates a saturated output signal S2 based on the output signal S1 from the gas sensor 101 at time t12. Incidentally, since an output signal of a gas increases in a certain trend, the saturated output signal S2 can be estimated from the time t11, the time t12, and the output signal S1. The time period from the start of the breath introduction to the calculation of the saturated output signal S2 is approximately 3 seconds.

As a method other than the above method, the following method may be used. A cover (not shown) is often provided around the sensor portion in the gas sensor 101. When the space in the cover is small, even if the amount of the introduced gas is small, the space in the cover can have the same concentration as the introduced gas. That is, the smaller the size of the space in the cover in the gas sensor 101, the shorter the time period until saturation. Accordingly, when the size of the space in the cover in the gas sensor 101 is small, the gas measurement processing section 513 may directly acquire the saturated output signal S2 without estimating the saturated output signal S2 from the output signal S1 as shown in FIG. 21. In the case of alcohol detection, the gas measurement processing section 513 acquires the output signals of the gas sensor for acetaldehyde 101d and the gas sensor for hydrogen 101f when the output signal of the gas sensor for alcohol 101c which is a target of the measurement reaches a peak value after waiting 3 to 5 seconds from the breath introduction. Then, the gas measurement processing section 513 may calculate the accurate gas saturated concentrations of alcohol, acetaldehyde, and hydrogen based on the saturated signal intensities directly acquired from the gas sensors 101c, 101d, and 101f by a concentration calculation based on a differential evolution method.

Incidentally, the time period from time t11 to time t12 is approximately 1 to 2 seconds. That is, the gas measurement can be achieved in a measurement of approximately 1 to 2 seconds, enabling a significant time saving.

As seen above, the breath inspection system Z using the moisture detection element 1 of the embodiment can achieve an inspection of a gas (for example, alcohol) within a very short time period.

Incidentally, the present invention is not limited to the above-mentioned embodiments, and encompasses various modifications. For example, the above-mentioned embodiments are described in detail for explaining the present invention in an easy-to-understand manner, and the present invention is not necessarily limited to an embodiment having all the configurations described herein. In addition, a part of configurations of one embodiment may be substituted by a configuration of another embodiment, or a configuration of one embodiment may be added to configurations of another embodiment. In addition, in a part of configurations of each embodiment, another configuration may be added, deleted, or substituted.

A part or all of the above-mentioned configurations, functions, sections 411, and 511 to 514, the storage devices 505, and the like may be realized by means of a hardware, for example, by designing them with an integrated circuit. As shown in FIG. 15 and FIG. 16, the above-mentioned configurations, functions, and the like may be realized by means of a software by allowing a processor, such as a CPU, to understand and execute programs for realizing the respective functions thereof. Information, such as programs, tables, and files, for realizing the respective functions may be stored in a storage device, such as a memory and a solid state drive (SSD), or in a recording medium, such as an integrated circuit (IC) card, a secure digital (SD) card, and a digital versatile disc (DVD) as well as in the HDD 602 as shown in FIG. 14.

Control lines and information lines that are considered to be required for explanation are shown in the embodiments, and all the control lines and information lines for a product are not always shown. Almost the all configurations may be considered to be practically connected to each other.

REFERENCE SIGNS LIST 1, 1a to 1d, 1C moisture detection element (moisture detection section)
2, 2a, 112 application electrode (application section)
3, 3a, 113 detection electrode (outputting section)
4, 4a to 4d, 114 insulating section
5 AC power source
11 water molecules
20a, 20b equivalent circuit
21 equivalent circuit of water molecules
100, 100a, 100b breath sensor (gas detection device)
101, 101a to 101f gas sensor (gas detection section)
120 substrate section
122 application electrode plate
123 detection electrode plate
131 through holes
201, 201a, 201b breath inspection device
202a, 202b breath introduction port
203 display section
211 steering wheel
300 breath detection device
301a, 301b A/D converter
400 measurement control device
403 input device
404 AC/AC invertor circuit
405 AC terminal
406 AC/DC converter circuit
407 DC terminal
500 analysis device
503 transmission/reception device
504 display device
511 processing section
512 moisture measurement processing section
513 gas measurement processing section
514 determination processing section
601 transmission device
602 storage device
C1, C2, Ca capacitor
Ra resistor
Z breath inspection system

The invention claimed is:

1. A moisture detection element comprising:
an insulating section made of an insulating material having a surface,
an application section to which a voltage is applied, and
an outputting section configured to output a voltage signal corresponding to a current flowing through an electrical path between the application section and the outputting section via water molecules adsorbed on the surface of the insulating material by the voltage applied to the application section, wherein the application section and the outputting section each include electrodes arranged on the surface of the insulating material
wherein the insulating section has projections and depressions provided on the surface on which the water molecules are adsorbed,
wherein the projections and depressions of the insulating section in the case of use in an environment at a temperature equal to or higher than a prescribed temperature are larger in magnitude than the projections and depressions of the insulating section in the case of use in an environment at a temperature equal to or lower than the prescribed temperature.

2. The moisture detection element according to claim 1, wherein the insulating section is configured to have a structure in which oxygen atoms are arranged at least on the surface thereof.

3. The moisture detection element according to claim 2, wherein the insulating section is made of an insulating metal oxide.

4. The moisture detection element according to claim 1, wherein the voltage applied to the application section is an AC voltage.

5. A gas detection device comprising
a moisture detection section according to claim 1 configured to detect moisture based on the voltage signal output by the outputting section of the moisture detection section, and
a gas measurement processing section that is placed around the moisture detection section and measures a concentration of a prescribed kind of gas.

6. The gas detection device according to claim 5, wherein the gas measurement processing section is at least one of an alcohol measurement section for measuring an alcohol concentration, a carbon monoxide measurement section for measuring a carbon monoxide concentration, a nitrogen monoxide measurement section for measuring a nitrogen monoxide concentration, an acetone measurement section for measuring an acetone concentration, an acetaldehyde measurement section for measuring an acetaldehyde concentration, and a hydrogen measurement section for measuring a hydrogen concentration.

7. A breath inspection system comprising the gas detection device of claim 5, and further comprising
a breath introduction section into which a breath can be introduced.

8. The breath inspection system according to claim 7, wherein the moisture detection section, the gas measurement processing section, and the breath introduction section are placed in a portable terminal.

9. The breath inspection system according to claim 7, wherein the moisture detection section, the gas measurement processing section, and the breath introduction section are placed in a steering wheel.

10. The breath inspection system according to claim 7, comprising an analysis section configured to acquire a signal from the moisture detection section and a signal from the gas measurement processing section for analysis, wherein the analysis section is configured to:
start acquisition of the signal from the gas measurement processing section when the signal acquired from the moisture detection section exceeds a first threshold,
stop acquisition of the signal from the gas measurement processing section when the signal acquired from the moisture detection section exceeds a second threshold which is larger than the first threshold, and
calculate a saturated concentration of the gas in the breath based on the signal value of the signal from the gas measurement processing section when the acquisition of the signal from the gas measurement processing section is started and the signal value of the signal from the gas measurement processing section when the acquisition of the signal from the gas measurement processing section is stopped,
wherein the gas is alcohol, acetaldehyde, and hydrogen, and the analysis section is configured to determine the presence or absence of alcohol drinking in a subject based on saturated concentrations of the alcohol, acetaldehyde, and hydrogen.

11. A moisture detection element comprising:
an insulating section made of an insulating material having a surface,
an application section to which a voltage is applied, and
an outputting section configured to output a voltage signal corresponding to a current flowing through an electrical path between the application section and the outputting section via water molecules adsorbed on the surface of the insulating material by the voltage applied to the application section, wherein the application section and the outputting section each include electrodes arranged on the surface of the insulating material, wherein
a first electrode has a rod shape,
a second electrode has a cylindrical shape that encloses the first electrode, and
a tabular section is connected to the first electrode and the second electrode, wherein
the tabular section includes the insulating section, the application section, and the outputting section,
one of the application section and the outputting section being connected to the first electrode,
the other of the application section and the outputting section being connected to the second electrode.

* * * * *